United States Patent [19]
Albert et al.

[11] Patent Number: 5,789,921
[45] Date of Patent: Aug. 4, 1998

[54] MAGNETIC RESONANCE IMAGING USING HYPERPOLARIZED NOBLE GASES

[75] Inventors: Mitchell S. Albert; Dilip Balamore. both of Shoreham, N.Y.; Gordon D. Cates, Jr., Skillman, N.J.; Bastiaan Driehuys, Bristol, Pa.; William Happer; Brian Saam, both of Princeton, N.J.; Arnold Wishnia, Setauket, N.Y.

[73] Assignees: The Research Foundation of State University of New York, Alabnay, N.Y.; The Trustees of Princeton University, Princeton, N.J.

[21] Appl. No.: 485,356

[22] Filed: Jun. 7, 1995

Related U.S. Application Data

[62] Division of Ser. No. 225,243, Apr. 8, 1995, Pat. No. 5,545, 396.

[51] Int. Cl.$^6$ ........................................... G01V 3/00
[52] U.S. Cl. ........................ 324/300; 324/304; 128/653.4
[58] Field of Search ........................... 324/300, 304, 324/312, 307, 309; 128/653.4, 654

[56] References Cited

U.S. PATENT DOCUMENTS

| | | | |
|---|---|---|---|
| 4,450,407 | 5/1984 | Kwon et al. | 324/304 |
| 4,586,511 | 5/1986 | Clark, Jr. | 128/653 |
| 4,775,522 | 10/1988 | Clark, Jr. | 424/9 |
| 4,793,357 | 12/1988 | Lindstrom | 128/654 |
| 4,862,359 | 8/1989 | Trivedi et al. | 364/413.05 |
| 4,996,041 | 2/1991 | Arai et al. | 424/9 |
| 5,357,959 | 10/1994 | Fishman | 128/653.4 |
| 5,433,196 | 7/1995 | Fiat | 128/653.4 |

OTHER PUBLICATIONS

Wyrwicz, A.M., Schofield, J.C., Tillman, P.C., Gordon, R.E., and Martin, P.A., *Science*, 222:428 (1983).
Miller, K.W., Reo, N.V., Uiterkamp, A.J.M.S., Stengle, D.P., Stengle, T.R., and Williamson, K.L., *Proc. Nat'l Acad. Sci. USA*, 78:4946 (1981).
Evers, A.S., Berkowitz, B.A., and d'Avignon, D.A., *Nature*, 328:157 (1987).
Wyrwicz, A.M., Li, Y.-E., and Schofield, J.C., *FEBS Lett.*, 162:334 (1983).
Burt, C.T., Moore, R.R., Roberts, M.F., and Brady, T.J., *Biochim. Biophys. Acta*, 805:375 (1984).
Burt, C.T., Moore, R.R., and Roberts, M.F., *J. Magn. Reson.*, 53:163 (1983).
Lockhart, S.H., Cohen, Y., Yasuda, N., Kim, F., Litt, L., Eger, E.I., Chang, L.-H., and James, T., *Anesthesiology*, 73:455 (1990).

(List continued on next page.)

*Primary Examiner*—Louis M. Arana
*Attorney, Agent, or Firm*—Hoffmann & Baron

[57] ABSTRACT

A method of imaging a spatial distribution of a noble gas by nuclear magnetic resonance spectrometry includes detecting a spatial distribution of at least one noble gas by NMR spectrometry and generating a representation of said spatial distribution of the noble gas. The noble gas is selected from noble gas isotopes having nuclear spin, preferably Xenon-129 and/or Helium-3. The noble gas is at least thermally or equilibrium polarized and is preferably hyperpolarized, most preferably hyperpolarized by optical (laser) pumping in the presence of an alkali metal or by metastability exchange. The generation of the representation of the noble gas spatial distribution includes at least one dimension, preferably 2 or 3 dimensions of the spatial distribution. The noble gas may be imaged according to the invention in chemical or biological systems, preferably in a human or animal subject or organ system or tissue thereof. Also, apparatus for nuclear magnetic resonance imaging of the spatial distribution of at least one noble gas includes means for imaging a noble gas by NMR spectrometry and means for providing and/or storing imageable quantities of a noble gas, preferably hyperpolarized Xenon-129 and/or Helium-3. Also, a medical composition includes a medically acceptable bifunctional gas effective for in vivo anesthesiological and NMR imaging functions, including at least one noble gas, preferably hyperpolarized Xenon-129 and/or Helium-3.

9 Claims, 7 Drawing Sheets

OTHER PUBLICATIONS

Mason, J., in *Multinuclear NMR*, Mason, J., ed., pp. 606–607, Plenum Press, New York (1987).

Barany, M., Spigos, D.G., Mok, E., Venkatasubramanian, P.N., Wilbur, A.C., and Langer, B.G., *Magn. Reson. Imaging*, 5:393 (1987).

Fullerton, G.D., and Cameron, I.L., Chapter 3 in *Biomedical Magnetic Resonance Imaging: Principles, Methodology, and Applications*, Wehrli, F.W., Shaw, D.S., and Kneeland, J.B., eds., pp. 115–155, VCH Publishers, New York (1988).

Susskind, H., Atkins, H.L., Klopper, J.K., Ansari, A.N., Richards, P., and Fairchild, R.G., *Prog. Nucl. Med.*, 5:144 (1978).

Susskind, H., Ellis, K.J., Atkins, H.L., Cohn, S.H., and Richards, P., *Prog. Nucl. Med.*, 5:13 1978).

Kendall, B.E. and Moseley, I.F., *J. Neuroradiology*, 8:3 (1981).

Imai, A., Meyer, J.S., Kobari, M., Ichijo, M., Shinohara, T., and Oravez, W.T., *Neuroradiology*, 30:463 (1988).

Yonas, H., Sekhar, L., Johnson, D.W., and Gur, D., *Neurosurgery*, 24:368 (1989).

Albert, M.S., Springer, C.S., Murphy, R., and Wishnia, A., *Abs., 11th Ann. Mtg. Soc. Magn. Reson. Med.*, 2104 (1992).

Albert, M.S., Springer, C.S., and Wishnia, A., *Abs., 11th Ann., Mtg. Soc. Magn. Reson. Med.*, 4710 (1992).

Jameson, C.J., Jameson, A.K., and Hwang, J.K., *J. Chem. Phys.*, 89:4074 (1988).

Carver, T.R., *Science*, 141:599 (1963).

Happer, W., Miron, E., Schaefer, S., Schreiber, D., van Wijngaarder, W.A., and Zeng, X., *Phys. Rev. A*, 29:3092 (1984).

Wagshul, M.E., and Chupp, T.E., *Phys. Rev. A*, 40:4447 (1989).

Wagshul, M.E., Thesis, Department of Physics, Harvard University (1991).

Grover, B.C., *Phys. Rev. Lett.*, 40:391 (1978).

Schaefer, S.R., Cates, G.D., Chien, T.-R., Gonatas, D., Happer, W., and Walker, T.G., *Phys. Rev. A*, 39:5613 (1989).

Schaefer, S.R., Cates, G.D., and Happer, W., *Phys. Rev. A*, 41:6063 (1990).

Schearer, L.D., in *Phys. Rev. Lett.*, 21:660 (1968).

Schearer, L.D., in *Phys. Rev.*, 188:505 (1969).

Schearer, L.D., in *Phys. Rev.*, 180:83 (1969).

Colegrove, F.D., Schearer, L.D., and Walters, G.K., *Phys. Rev.*, 132:2561 (1963).

Hadeishi, T., and Liu, C.-H., *Phys. Rev. Lett.*, 19:211 (1967).

Schearer, L.D., *Phys. Lett.*, 28A:660 (1969).

Cates, G.D., Benton, D.R., Gatzke, M., Happer, W., Hasson, K.C., and Newbury, N.R., *Phys. Rev. Lett.*, 65:2591 (1990).

Gatzke, M., Cates, G.D., Driehuys, B., Fox, D., Happer, W., and Saam, B., *Phys. Rev. Lett.*, 70:690 (1993).

Bhaskar, N.D., Happer, W., and McClelland, T., *Phys. Rev. Lett.*, 49:25 (1982).

Cates, G.D., Fitzgerald, R.J., Barton, A.S., Bogorad, P., Gatzke, M., Newbury, N.R., and Saam, B., *Phys. Rev. A*, 45:4631 (1992).

Raftery, D., Long, H., Meersmann, T., Grandinetti, P.J., Reven, L. and Pines, A., *Phys. Rev. Lett.*, 66:584 (1991).

Raftery, D., Long, H., Reven, L., Tang, P., and Pines, A., *Chem. Phys. Lett.*, 191:385 (1992).

Long, H.W. Gaede, H.C., Shore, J., Reven, L., Bowers, C.R., Kritzenberger, J., Pietrass, T., and Pines, A., *J. Am. Chem. Soc.*, 115:8491 (1993).

Rinck et al., *An Introduction to Magnetic Resonance in Medicine* (1990).

Stark et al., eds., *Magnetic Resonance Imaging*, vol. 1, 2d ed. (1992) Chapters 1 and 2.

Hunt E.R., and Carr, H.Y., *Phys. Rev.*, 130:2302 (1963).

Tilton, Jr., R.F., and Kuntz, Jr., I.D., *Biochemistry*, 21:6850 (1982).

Diehl, P., and Jokisaari, J., *J. Magn. Reson.*, 88:669 (1990).

Cullen, S.C., and Gross, E.G., *Science*, 113:580 (1951).

Wilcock, R.J., Battino, R., Danforth, W.F., and Wilhelm, E., *J. Chem. Thermodyn.*, 10:317 (1978).

Blumgart, H.L., and Weiss, S., *J. Clin. Invest.*, 4:339–425 (1927).

Pollack, G.L., Himm, J.F., and Enyeart, J.J., *J. Chem. Phys.*, 81:3239 (1984).

Wishnia, A., *Biochemistry*, 8:5064 (1969).

Bouchiat, M.A., Carver, T.R., and Varnum, C.M., *Phys. Rev. Lett.*, 5:373 (1960).

Zeng, X., Wu, Z., Call, T., Miron, E., Schreiber, D., and Happer, W., *Phys. Rev. A*, 31:260 (1985).

Laloe, F., Nacher, P.J., Leduc, M., and Schearer, L.D., *AIP Conf. Proc.* #131 (Workshop on Polarized $^3$He Beams and Targets) (1984).

Ernst et al., *Principles of Nuclear Magnetic Resonance in One and Two Dimensions* (1987).

Wehrli, F.W., et al., eds., *Biomedical Magnetic Resonance Imaging* (1988).

Schoenborn, B.P., *Nature*, 208:760 (1965).

Moschos, A., and Reisse, J., *J. Mag. Reson.*, 95:603 (1991).

Yonas, H., Laligam, S., Johnson, D.W., and Gur, D., *Neurosurgery*, 24:368 (1989).

Manabe, A., Miyazaki, T., and Toyoshima, H., *Magn. Reson. in Med.*, 5:492–501 (1987).

Haase, A., Frahm, J., Matthaei, D., Hanicke, W., and Merboldt, K.D., *J. Magn. Reson.*, 67:217 (1986).

Look, D.C., and Locker, D.R., *Rev. Sci. Instrum.*, 41:250–251 (1970).

Norberg, R.E., in *Rare Gas Solids*, eds. Hohler, G., Springer-Verlag, New York (1984).

Yen, W.M., and Norberg, R.E., *Phys. Rev.*, 131:269 (1963).

Kaplan, H.M., Brewer, N.R., and Blair, W.H., in *The Mouse in Biomedical Research*, eds. Foster, H.L., Small, J.D., and Fox, J.G., pp. 248–278, Academic Press, New York (1983).

Knudsen, G.M., Pettigrew, K.D., Patlak, C.S., and Paulson, O.B., *Am. J. Physiol.*, In Press.

Kanal, E., and Wehrli, F.W., Chapter 2 in *Biomedical Magnetic Imaging*, Wehrli, F.W., Shaw, D., and Kneeland, J.B., eds., pp. 47–112, VCH Publishers, New York (1988).

Pollack, G.L., and Himm, J.F., *J. Chem. Phys.*, 77:3221–3229 (1982).

Robillard, Jr., K.A., and Wishnia, A., *Biochemistry*, 11:3835–3840 (1972).

Albert et al., *Chem. Abstracts* 121:128933r (1994).

Pfeffer, M., *Chem. Abstracts* 121:174319 (1994).

MAGNETIC RESONANCE IMAGING USING HYPERPOLARIZED NOBLE GASES

This is a divisional of application Ser. No. 08/225,243 filed on Ap. 8, 1995, now U.S. Pat. No. 5,545,396.

This invention was made with government support under Grant No. 431-4735A, awarded by the National Science Foundation, and Grant Nos. 88-0165 and F49620-92-J-02 11, awarded by the Air Force Office of Scientific Research. The government has rights in this invention.

BACKGROUND OF THE INVENTION

The present invention relates generally to techniques of nuclear magnetic resonance imaging. In particular, the present invention relates to, among other things, the detection and imaging of a noble gas by nuclear magnetic resonance spectrometry.

Current views as to the molecular basis of anesthetic action are mostly derived from experimental work carried out in vitro. Interpretation of many of the results of these studies are extremely controversial, e.g., changes in lipid structure are observed at exceedingly high, indeed toxic, concentrations of anesthetic. Changes observed in vitro, from animals whose physiology has been altered, or from animals administered non-clinical doses of anesthetics might not reflect the effects of these agents clinically. It is believed that significant progress can be made by employing direct non-invasive methods for the detection and characterization of anesthetics in living animals. Both lipid solubility and protein binding undoubtedly do play a role, but new ideas are now needed.

Attempts have been made to bring powerful nuclear magnetic resonance (NMR) techniques to bear on this problem. (References 1-3). Wyrwicz and co-workers pioneered the use of fluorine-19 ($^{19}F$) NMR spectroscopy to observe fluorinated anesthetics in intact tissues and recorded the first $^{19}F$ NMR spectra from the brain of a live anesthetized rabbit. (References 1, 4). These early studies demonstrated the feasibility of studying the fate of anesthetics in live mammals. Burt and collaborators also used halothane and other fluorinated anesthetics for monitoring membrane alterations in tumors by $^{19}F$ NMR. (References 5-6). In recent years, several groups have conducted $^{19}F$ NMR studies which have shed light on the molecular environment of anesthetics in the brains of rabbits and rats. (References 3, 7). Using a surface coil placed on top of the calvarium during halothane inhalation, two overlapping spectral features observed by d'Avignon and coworkers, perhaps 0.1-0.2 ppm apart, could be resolved through their different transverse relaxation times ($T_2$). (Reference 3). The biexponential dependence of the spin-echo amplitude on echo delay reported in this study demonstrated that anesthetics in different molecular environments could be discerned in the brain in vivo using $^{19}F$ NMR. Such environments, separated by chemical shifts of only about 0.1 ppm, had previously been reported by Wyrwicz et al. in high resolution studies of excised neural tissue. (Reference 4).

Notwithstanding such attempts to use other compounds for NMR imaging, state-of-the-art biological magnetic resonance imaging (MRI) has remained largely restricted to the water proton, $^{1}H_2O$, NMR signal. The natural abundance of water protons, about 80-100M in tissue, and its large magnetic moment make it ideal for most imaging applications. Despite its tremendous value as a medical diagnostic tool, however, proton MRI does suffer several limitations. Most notably, the water protons in lung tissue, and the protons in lipids of all interesting biological membranes, are notoriously NMR invisible as a result of the short $T_2$ in such environments. (References 8-9). Other $^{1}H$ signals and signals from other biologically interesting nuclides are either present in too low a concentration ($10^{-3}$ to $10^{-1}M$, compared to ca. 100M for $H_2O$) or have undesirable NMR characteristics. In studying dynamic processes with $^{1}H_2O$, one must sacrifice much of the proton signal to exploit differences in effective spin density resulting from $T_1$ and/or $T_2$ spatial variation. (Reference 10).

Various noble gases are known to be effective anesthetic agents. For example, Xenon is approved for use in humans, and its efficacy as a general anesthetic has been shown. Attempts have previously been made to take advantage of the properties of Xenon for purposes of medical imaging, but success has heretofore been extremely limited, and techniques have been impractical at best. For example, the $^{127}Xe$ isotope was used in early ventilation studies of the lung. (References 11-12). Unfortunately, the poor image quality attained limited its clinical use. Xenon has, however, been used as a contrast enhancement agent in computed tomography (CT) studies of the brain, (References 13-14), and as a tracer for regional cerebral blood flow (rCBF) measurements. (Reference 15).

An isotope of Xenon, Xenon-129 ($^{129}Xe$), has non-zero nuclear spin (i.e., ½) and therefore is a nucleus which, in principle, is suited to study by nuclear magnetic resonance techniques. Despite the apparent potential for use of Xenon in magnetic resonance imaging, its small magnetic moment, and the low number densities of gas generally achievable, have heretofore been insuperable obstacles to practicable magnetic resonance (MR) imaging of $^{129}Xe$ at normal, equilibrium (also known as "Boltzmann") polarizations, P (P-$10^{-5}$ in 0.5-1.5 Tesla (T) clinical imaging systems). However, unlike the water proton ($^{1}H$) employed as the nucleus in conventional NMR techniques, the nuclear magnetic resonance signals obtainable from $^{129}Xe$ are extraordinarily sensitive to local environment and therefore very specific to environment.

Certain aspects of the behavior of $^{129}Xe$, and other noble gas isotopes having nuclear spin, in various environments have been studied and described. For example, Albert et al. have studied the chemical shift and transverse and longitudinal relaxation times of Boltzmann polarized $^{129}Xe$ in several chemical solutions. (Reference 16). Albert et al. and others have also shown that Oxygen can affect longitudinal relaxation time $T_1$ of $^{129}Xe$. (References 17-18). Miller et al. have also studied the chemical shifts of $^{129}Xe$ and $^{131}Xe$ in solvents, proteins, and membranes. (Reference 2). However, none of these publications provides any indication of a method by which $^{129}Xe$ could be used for nuclear magnetic resonance imaging.

It is known in the art that the polarization of certain nuclei, such as noble gas nuclei having nuclear spin, may be enhanced over the equilibrium or Boltzmann polarization, i.e., hyperpolarized. Such techniques include spin exchange with an optically pumped alkali metal vapor and metastability exchange.

The physical principles underlying the hyperpolarization of noble gases have been studied. (Reference 19). For example, Happer et al. have studied the physics of spin exchange between noble gas atoms, such as Xenon, with alkali metals, such as Rubidium. (Reference 20). Others have studied spin exchange between Helium and alkali metals. (References 21-22, 49). Other publications have described physical aspects of spin exchange between alkali metals and noble gases. (References 23–24). The technique of using metastability exchange to hyperpolarize noble gases has been studied by Schearer et al. and by Hadeishi et al. (References 26–31).

Other publications, by Cates et al. and Gatzke et al., describe certain behaviors of frozen, crystalline $^{129}$Xe that has been hyperpolarized. (References 32–33). Cates et al. and others describe spin-exchange rates between Rubidium and $^{129}$Xe at high Xenon pressures as measured by magnetic resonance apparatus. (References 34–35). These publications, however, relate to $^{129}$Xe behavior in highly controlled physical systems and provide no description concerning how $^{129}$Xe might be used to produce images by nuclear magnetic resonance.

Raftery et al. have described optically pumped $^{129}$Xe as an adsorption probe for the study of surface structure by analysis of NMR spectra. (References 36–37). Long et al. have also observed the chemical shift of laser polarized Xenon adsorbed to a polymer surface. (Reference 38).

U.S. Pat. Nos. 4,856,511 and 4,775,522 to Clark describe a nuclear magnetic resonance technique for detecting certain dissolved gases in an animal subject. Gas compositions described as useful for this technique include fluorine compounds such as perfluorocarbons. Other gases suggested to be potentially useful for the technique of Clark include $^{129}$Xe, but Clark fails to recognize any of the difficulties which have heretofore rendered use of $^{129}$Xe for magnetic resonance imaging of biological subjects impracticable.

Therefore, it would be a significant advance in the art to overcome the above-described difficulties and disadvantages associated with nuclear magnetic resonance imaging, in a manner which would permit the imaging of noble gases, especially the imaging of noble gases in biological systems, without requiring excessively long image acquisition times and without being limited to systems and environments previously imageable only by $^1$H NMR.

SUMMARY OF THE INVENTION

In accordance with the present invention, there is provided a method of performing nuclear magnetic resonance imaging which includes detecting the spatial distribution of at least one noble gas by nuclear magnetic resonance (NMR), and generating a representation of the noble gas spatial distribution.

In a preferred embodiment, there is also provided a method of performing nuclear magnetic resonance imaging of an animal or human subject by administering an imageable amount of at least one noble gas to the subject, employing an NMR imaging spectrometer to detect radiofrequency signals derived from the magnetic resonance of at least one noble gas, processing the detected signals to obtain an NMR parameter data set as a function of the spatial distribution of at least one noble gas, and further processing the data set to generate a representation of at least one dimension of the spatial distribution of at least one noble gas.

In another preferred embodiment, the method of the invention further includes detecting and imaging at least one hyperpolarized noble gas. The hyperpolarized noble gas is preferably hyperpolarized by laser polarization through spin exchange with an alkali metal or by metastability exchange. The noble gas is preferably selected from among Helium-3, Neon-21, Krypton-83, Xenon-129, Xenon-131 and mixtures thereof. Most preferably, the noble gas is Helium-3 or Xenon-129. Combinations of noble gases and/or noble gas isotopes are contemplated, as are combinations of hyperpolarized and non-hyperpolarized noble gases and/or noble gas isotopes. When the noble gas is laser polarized through spin exchange with an alkali metal, preferably an alkali metal selected from among Sodium-23, Potassium-39, Cesium-133, Rubidium-85, and Rubidium-87. Most preferably, the alkali metal is Rubidium-85 or Rubidium-87.

The method of the invention preferably includes detecting and imaging at least one physical dimension of the spatial distribution of at least one noble gas, more preferably including detecting and imaging two or three physical dimensions. The method of the invention may also include detecting and imaging alterations of the spatial distribution of the noble gas as a function of time.

The generating of a representation of a noble gas preferably includes generating a representation of at least one physical dimension of the spatial distribution of the noble gas, more preferably including generating a representation of two or three physical dimensions of the noble gas. The generating of the representation may also include generating a representation of one or more physical dimensions of the spatial distribution of the noble gas as a function of time, including such NMR parameters as chemical shift, $T_1$ relaxation, $T_2$ relaxation, and $T_{1\rho}$ relaxation. Preferably, the method of the invention includes generating a visual representation.

The noble gas being imaged is preferably distributed spatially in at least one physical phase such as a gas, liquid, gel, or solid. The noble gas may be imaged as distributed in two or more physical phases in one sample. The noble gas being imaged may be distributed on a solid surface. The noble gas may be imaged in association with various materials or environments.

The sample being imaged using a noble gas may include an in vitro chemical, in vitro biological or in vivo biological, system. When the noble gas distribution in an in vivo biological system is imaged, the system may include one or more human or animal subjects. The noble gas is preferably distributed in an organ or body system of the human or animal subject. Alternatively, the noble gas may be distributed in an anatomical space of the subject.

In another embodiment of the invention, there is provided a medical composition which includes a medically acceptable bifunctional gas effective for in vivo anesthesiological and nuclear magnetic resonance imaging functions. In a preferred embodiment, the gas composition includes at least one noble gas, preferably selected from among Helium-3, Neon-21, Krypton-83, Xenon-129, and Xenon-131. More preferably, the noble gas is Helium-3 or Xenon-129. The noble gas is preferably hyperpolarized, more preferably through spin exchange with an alkali metal or through metastability exchange. Combinations of hyperpolarized and non-hyperpolarized noble gases and noble gas isotopes are possible.

Also in accordance with the present invention, there is provided apparatus for nuclear magnetic resonance imaging which includes NMR imaging means, for detecting and imaging at least one noble gas, and means for providing imageable quantities of the noble gas. In a preferred embodiment, the apparatus includes means for providing imageable quantities of a hyperpolarized noble gas. The apparatus of this embodiment includes hyperpolarizing means, preferably means for hyperpolarizing a noble gas through spin exchange with an alkali metal or through metastability exchange. The noble gas may be provided in continuous, discontinuous, and/or quasi-continuous mode, and when more than one noble gas is provided, noble gases may be provided as a mixture or individually, and may be provided either together or by separate routes and/or at separate times and durations.

The noble gas may be contacted with the sample to be imaged in gaseous, liquid, or solid form, either alone or in combination with one or more other components in a gaseous, liquid, or solid composition. The noble gas may be combined with other noble gases and/or other inert or active components. The noble gas may be delivered as one or more boluses or by continuous or quasi-continuous delivery.

Also in accordance with the invention there is provided a method of performing nuclear magnetic resonance imaging of a human or animal subject. In this embodiment, the method includes administering to a subject an imageable amount of a hyperpolarized noble gas, generating radio-frequency signals from the nuclear magnetic resonance of the hyperpolarized noble gas by means of a nuclear magnetic resonance imaging spectrometer, detecting the generated radio-frequency signals, processing the detected radio-frequency signals to derive a nuclear magnetic resonance parameter data set as a function of a spatial distribution of the hyperpolarized noble gas in the subject, and further processing said nuclear magnetic resonance parameter data set to derive a representation corresponding to at least one spatial dimension of the spatial distribution of the hyperpolarized noble gas in the subject.

The noble gas may be administered to a human or animal subject as a gas or in a liquid, either alone or in combination with other noble gases and/or other inert or active components. The noble gas may be administered as a gas by either passive or active inhalation or by direct injection into an anatomical space such as lung or gastrointestinal tract. The noble gas may be administered as a liquid by enteral or parenteral injection. The preferred method of parenteral administration includes intravenous administration, optionally by contacting blood with the noble gas extracorporeally and reintroducing the noble gas-contacted blood by intravenous means.

The present invention solves the disadvantages inherent in the prior art by providing a method for imaging at least one noble gas by nuclear magnetic resonance. The present method provides a new and unexpectedly powerful method of NMR imaging of noble gas spatial and temporal distribution in non-biological as well as in in vitro and in vivo biological systems. The present invention also permits the acquisition of images of high signal to noise ratio, in unexpectedly short acquisition periods. In addition, the present invention provides a method for imaging biological phenomena of short duration as well as for imaging systems previously not amenable to imaging by conventional $^1$H NMR techniques.

Other objects and advantages of the present invention will become more fully apparent from the following disclosure, figures, and appended claims.

DETAILED DESCRIPTION OF THE PREFERRED EMBODIMENTS

Figure 1A:
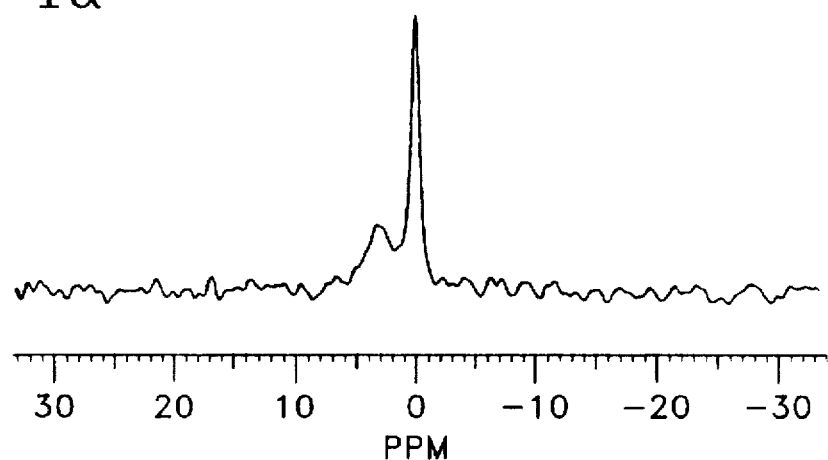
FIG. 1a shows a nuclear magnetic resonance spectrum of $^{129}$Xe in a rat brain synaptosome suspension.

Nuclear magnetic resonance spectroscopy is a technique which is well known in a wide variety of scientific disciplines. Basic considerations regarding the conventional practice of nuclear magnetic resonance imaging, especially as applied to biological systems, are found in Rinck et al., *An Introduction to Magnetic Resonance in Medicine* (1990), especially Chapters 1–4 (Reference 39); and Wehrli, F. W., "Principles of Magnetic Resonance", Chapter 1, and Wood, M. L., "Fourier Imaging", Chapter 2, in *Magnetic Resonance Imaging*, Vol. 1, 2d ed., Stark et al., eds. (1992) (Reference 40). These publications are incorporated by reference herein. In certain disciplines, an adaptation of NMR spectroscopy, involving the generation of images from NMR data has found increasing popularity. In medicine, certain MRI techniques have become fairly commonplace, principally employing the water proton ($^1$H$_2$O) for the imaging of certain regions in the body.

Nonetheless, certain other magnetically susceptible nuclei are desired to be adapted for MRI for various reasons. In particular, the physical characteristics of other elements may predispose the nuclei to the imaging of other kinds of physical and biological systems. In medicine, other nuclei are desired which can enable the imaging of regions of the body which are difficultly accessible by currently available NMR probes. Prior to the unexpected observations of the utility of noble gases for MRI applications, as described herein, acceptable alternative nuclear probes have been unavailable.

Noble gas isotopes having non-zero nuclear spin have now been discovered to offer vast possibilities for use in MRI. For example, the $^{129}$Xe isotope is, in principle, suited to NMR uses, but is 26% naturally abundant and has a sensitivity relative to $^1$H (in conventional NMR) of 2.12× 10$^{-2}$. The resonance frequency of $^{129}$Xe spans an enormous range (0–300 ppm) over the gas and condensed phase, and is exceptionally sensitive to chemical environment. (Reference 2). Its longitudinal relaxation time, $T_1$, is huge (practically at least 3000 s in the pure gas phase, and theoretically perhaps as long as 56 hrs at 1 atm), (References 32, 41), and is particularly sensitive to chemical environment, O$_2$ concentration, (References 17–18), and the effects of other relaxation promoters. (References 2, 42, 16). Its transverse relaxation time is also susceptible to relaxation promoters. (References 16, 18, 43).

The longitudinal and transverse relaxation times, $T_1$ and $T_2$, respectively, are also indicative of the environment surrounding the $^{129}$Xe atom, e.g., whether the atom is bound to a protein, dissolved in a lipid, or constrained in some other way. Thus a combination of chemical shift, $T_1$, and $T_2$ data can provide a basis for distinguishing the presence or absence of the nucleus in a particular environment as well as for identifying the nature of the environment in question.

Elemental Xenon is a benign and effective anesthetic, (Reference 44), which is not metabolized by the body. Xenon has an essentially Raoult's Law solubility in nonpolar solvents. (Reference 45). Inhaled into the lungs, Xenon equilibrates quickly with the pulmonary circulation, reaching a steady state with the entire blood volume in one blood circuit, (Reference 13), on average, about 1 s or 1–2 breaths in the mouse, about 18 s in humans. (Reference 46). Xenon is known to accumulate rapidly in highly-vascularized tissue. For example, in the brain, which contains 10% lipid and 10% protein, (Reference 10), one can expect steady-state concentrations (for 0.5–1.0 atm lung Xenon) of 5–10 mM in the membrane bilayers, 2–4 mM in water, and about 1–5 mM bound to proteins. (References 45, 47–48). Xenon is also approximately twice as soluble in white matter as in gray matter. (Reference 13). The NMR resonance frequency of $^{129}$Xe is different in each of the above sites, and exchange between compartments is slow on the chemical shift NMR timescale. (References 2, 16–17). The potential usefulness of hyperpolarized $^{129}$Xe as a contrast agent in biological systems is therefore apparent.

The total Xenon concentration in materials of biological interest will typically range between about two and about five times its solubility in pure water. The problem with any attempt to image Boltzmann polarized Xenon in such a system is that many samples are required in order to determine a solution parameter. These difficulties stem in large part from the lower concentrations of $^{129}$Xe, its smaller magnetic moment, and its lower natural abundance, as compared with $^1H_2O$. Similar considerations apply with regard to other noble gases which are generally less soluble in water as well as in nonpolar media.

Figure 1B:
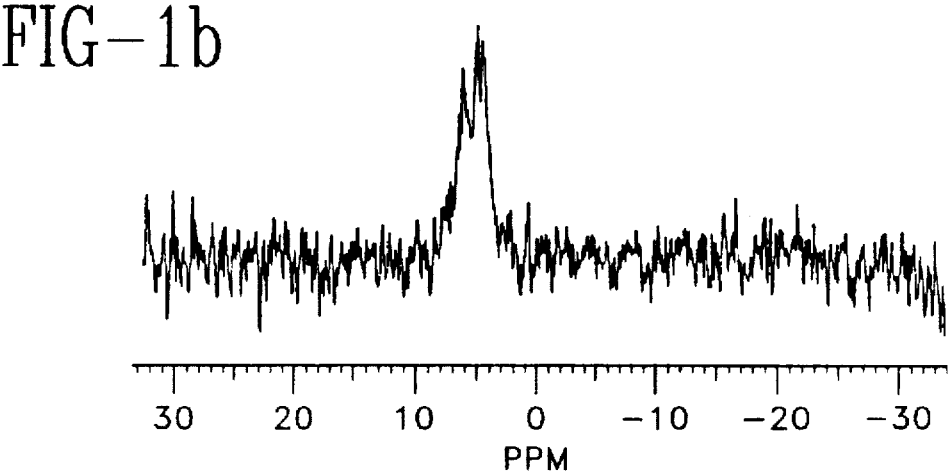
FIG. 1b shows a nuclear magnetic resonance spectrum of $^{129}$Xe in a homogenate of rat brain tissue.
Figure 1C:
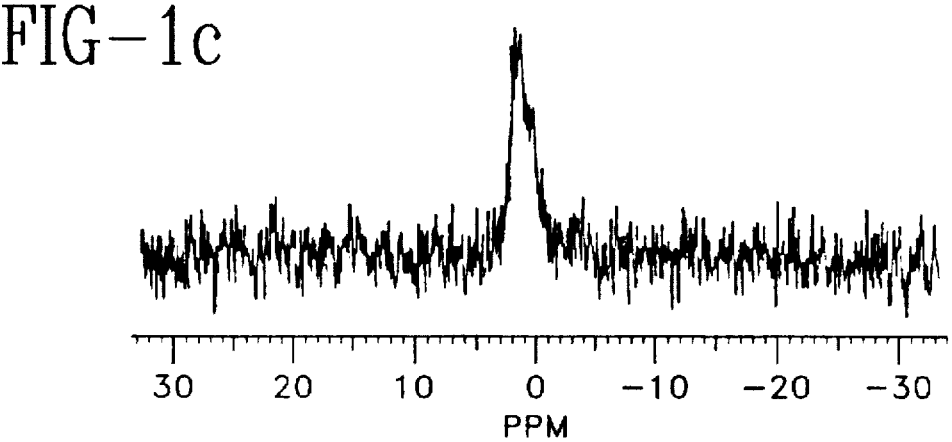
FIG. 1c shows a nuclear magnetic resonance spectrum of $^{129}$Xe in a whole rat brain preparation.

For example, the spectrum of FIG. 1c, obtained in 8 hrs from in vitro brain samples taken from rats anesthetized with Xenon gas, has significantly less signal to noise (S/N) than a spectrum of $^{129}$Xe in a synaptosomal suspension shown in FIG. 1a, obtained in 27 hrs under a Xe pressure of 3 atm.

The difficulties which have heretofore prevented the development of noble gas MRI are clear: typically long longitudinal relaxation times and low signal strength require signal averaging of exceedingly many free induction decays (FIDS) over long periods of time. It is clear that to conduct in vivo NMR experiments, extraordinary enhancement of the noble gas signal is necessary. The total accumulation times for Boltzmann noble gas spectra is prohibitively long in such biological samples.

The ability to use noble gases for NMR imaging, then, is directly and profoundly limited by the average signal intensity and the signal acquisition ability of the spectrometer. Given current NMR spectrometer technology, it is reasonable to conclude that on the order of a 10,000 fold increase in sensitivity, e.g., that increase necessary to render Xenon imaging possible using Boltzmann polarized Xenon, could take years if not decades to develop, assuming it is feasible at all. The required sensitivity increase is more practicably attained through hyperpolarization, for example, through the use of optical pumping and spin exchange, (References 21–22, 32, 36), or metastability exchange. (References 26–31). This method of enhancing the noble gas signal can be used to create noble gas nuclear polarizations which are on the order of $10^4$–$10^6$ larger than typical thermal equilibrium polarizations. Nuclear polarizations attained using these techniques are easily of order 0.25, (Reference 32), and can approach 1.0, making the product of spin density and polarization at least an order of magnitude larger than for the proton ($^1H$) in typical imaging situations. Thus, it has now been unexpectedly found that the hyperpolarization of noble gases permits a spectacular new means of producing magnetic resonance images.

While the extraordinary property of hyperpolarizability of noble gases, especially $^{129}$Xe and $^3$He, is of great importance in rendering the imaging of biological systems possible, other factors play a role in developing such images. For example, noble gases exhibit other unusual properties, including distinctly different behavior compared to $^1H_2O$ in (a) cell and tissue compartmentalization; (b) dramatically time-dependent distribution; and (c) response of resonance frequency, $T_1$, and $T_2$ to environment, $O_2$ concentration and subcellular exchange kinetics. The combination of hyperpolarizability of noble gases and these other unusual properties enables the use of noble gases as a new and qualitatively different source of NMR image contrast. For example, as opposed to water protons, $^{129}$Xe is not omnipresent; its space and time distribution in the body depends entirely on the anatomy and physiology of Xenon transport. (Reference 13). This permits its use in magnetic resonance imaging (MRI) and magnetic resonance spectrometry (MRS) studies of soft-tissue anatomy, physiology (e.g., cerebral blood flow, cerebral activity) and pathology (e.g., demyelination, early detection of tumors or other foci of changed or anomalous metabolism). Moreover, the large MR signal strengths obtainable using hyperpolarized noble gases permit the use of the high-speed imaging protocols, which have heretofore been possible only with $^1H_2O$.

The imaging method of the invention is preferably performed using the $^{129}$Xe and/or the $^3$He nuclei. However, the method of the invention may also be performed with other noble gases, i.e., other noble gas isotopes having nuclear spin. $^3$He, $^{129}$Xe and the other noble gases may be preferred in different applications because of their different physical and magnetic resonance properties. A list of noble gas nuclei useful according to the invention is provided below in Table I. This list is intended to be illustrative and non-limiting.

TABLE I

| Hyperpolarizable Noble Gases | | |
|---|---|---|
| Isotope | Natural Abundance (%) | Nuclear Spin |
| $^3$He | ~$10^{-6}$ | 1/2 |
| $^{21}$Ne | 0.27 | 3/2 |
| $^{83}$Kr | 11.5 | 9/2 |
| $^{129}$Xe | 26.4 | 1/2 |
| $^{131}$Xe | 21.2 | 3/2 |

While each of the noble gas isotopes listed in Table I, alone or in combination, may be used for nuclear magnetic resonance imaging according to the invention, it is known that the degree of polarization of the gases in equilibrium (Boltzmann) state is prohibitively low, preventing high speed image acquisition. The various parameters governing signal decay such as $T_1$ and $T_2$ relaxation and the local environment of the nucleus will also determine whether high speed images can be effectively acquired. These limitations become of great importance in acquisition of images from in vitro and in vivo biological systems since the time course of events desired to be imaged often requires data acquisition periods of less than one second. Enhancement of the NMR signal is, therefore, highly desirable. Accordingly, the noble gas is preferably hyperpolarized relative to its normal Boltzmann polarization. Such hyperpolarization is preferably induced prior to data acquisition by an NMR spectrometer and may be induced by any of the techniques known in the art.

Further enhancement of the noble gas magnetic resonance signal may be obtained, independently of, or together with, hyperpolarization, by increasing the proportion of the imageable isotope in each noble gas to a level above the natural abundance of such imageable isotopes in the noble gas. In the case of $^{129}$Xe, which has a natural isotopic abundance of about 26%, this amounts to enhancement by no more than a factor of four, even in a gas which is enriched to 100% $^{129}$Xe, other considerations, such as the hyperpolarizability of the noble gas, usually play a much larger role in signal enhancement, but isotopic enrichment can provide a significant contribution to the ultimate efficacy of the present invention. This is especially true in the case of $^3$He which has a natural abundance of on the order of $10^{-6}$. Even the hyperpolarizability of $^3$He and its very large magnetic resonance signal could be considerably offset by the low natural abundance of this isotope. Despite its low natural abundance, however, $^3$He is readily available in very pure form as a result of industrial use of tritium ($^3$H), which decays exclusively to $^3$He. The ready availability of artificial sources of $^3$He eliminates concerns regarding its low natural abundance and associated expensive enrichment processes.

Noble gases may be hyperpolarized for use according to the invention through any of various means known in the art, such as spin-exchange interactions with optically pumped alkali metal vapor. (References 34–35, 49–50). The optical pumping and spin-exchange can be performed in the absence of an applied magnetic field, but is preferably performed using modest fields of about 1 G or larger. Pumping in the NMR magnet bore at fields of several Tesla is also possible. The maximum steady state $^{129}$Xe nuclear polarization achievable depends on the time constant characterizing the spin exchange with the alkali metal and the time constant characterizing the relaxation ($T_1$) due, for example, to contact with the surfaces of the pumping cell. For instance, with $T_1 \approx 20$ min, polarizations of 20–40% are quite practicable, (Reference 32), and polarizations of 90% or more should be attainable. The long $T_1$ of the gas also allows samples to be manipulated, even stored as Xe ice, (Reference 32), and transported on time scales of hours or even days, without serious loss of magnetization.

The art of hyperpolarizing noble gases through spin exchange with an optically pumped alkali-metal vapor starts with the irradiation of the alkali-metal vapor with circularly polarized light at the wavelength of the first principal ($D_1$) resonance of the alkali metal (e.g. 795 nm for Rb). The $^2S_{1/2}$ ground state atoms are thus excited to the $^2P_{1/2}$ state and subsequently decay back to the ground state. If performed in a modest (10 Gauss) magnetic field aligned along the axis of incident $D_1$ light, this cycling of atoms between the ground and first excited states leads to nearly 100% polarization of the atoms in a few microseconds. This polarization is carried mostly by the lone valence electron characteristic of all alkali metals; this essentially means that all of these electrons have their spin either aligned or anti-aligned to the magnetic field depending upon the helicity (right- or left-handed circular polarization state) of the pumping light. If a noble gas with non-zero nuclear spin is also present, the alkali-metal atoms can undergo collisions with the noble gas atoms in which the polarization of the valence electrons is transferred to the noble-gas nuclei through a mutual spin flip. This spin exchange results from the Fermi-contact hyperfine interaction between the electron and the noble-gas nucleus. By maintaining the alkali-metal polarization at nearly 100% with the pumping light, large non-equilibrium polarizations (5%–80%) are currently achievable in large quantities of a variety of noble gases through this spin-exchange process. For example, one currently available Titanium:Sapphire-laser could theoretically provide 1 g/hr (200 cc-atm/hr) of highly polarized $^{129}$Xe.

The alkali metals capable of acting as spin exchange partners in optically pumped systems include any of the alkali metals. Preferred alkali metals for this hyperpolarization technique include Sodium-23, Potassium-39, Rubidium-85, Rubidium-87, and Cesium-133. Alkali metal isotopes, useful according to the invention, and their relative abundance and nuclear spins are listed in Table II, below. This list is intended to be illustrative and non-limiting.

TABLE II

Alkali Metals Capable of Spin Exchange

| Isotope | Natural Abundance (%) | Nuclear Spin |
|---------|----------------------|--------------|
| $^{23}$Na | 100 | 3/2 |
| $^{39}$K | 93.3 | 3/2 |
| $^{85}$Rb | 72.2 | 5/2 |
| $^{87}$Rb | 27.8 | 3/2 |
| $^{133}$Cs | 100 | 7/2 |

Alternatively, the noble gas may be hyperpolarized using metastability exchange. (References 28, 51). The technique of metastability exchange involves direct optical pumping of, for example, $^3$He, without need for an alkali metal intermediary. The method of metastability exchange usually involves the excitation of ground state $^3$He atoms ($1^1S_0$) to a metastable state ($2^3S_1$) by weak radio frequency discharge. The $2^3S_1$ atoms are then optically pumped using circularly polarized light having a wavelength of 1.08 μm in the case of $^3$He. The light drives transitions up to the $2^3P$ states, producing high polarizations in the metastable state to which the $2^3P$ atoms then decay. The polarization of the $2^3S_1$ states is rapidly transferred to the ground state through metastability exchange collisions between metastable and ground state atoms. Metastability exchange optical pumping will work in the same low magnetic fields in which spin exchange pumping works. Similar polarizations are achievable, but generally at lower pressures, e.g., about 0–10 Torr.

The method of the invention preferably includes detecting and imaging at least one physical dimension of the spatial distribution of at least one noble gas, more preferably including detecting and imaging two or three physical dimensions. The method of the invention may also include detecting and imaging alterations in the spatial distribution of the noble gas as a function of time.

The generating of a representation of a noble gas preferably includes generating a representation of at least one physical dimension of the spatial distribution of the noble gas, more preferably including generating a representation of two or three physical dimensions of the noble gas. The generating of the representation may also include generating a representation of one or more physical dimensions of the spatial distribution of the noble gas as a function of time, including such NMR parameters as chemical shift, $T_1$ relaxation, $T_2$ relaxation and $T_{1\rho}$ relaxation; Preferably, the method of the invention includes generating a visual representation.

Representations of the spatial distribution of a noble gas may be generated by any of the methods known in the art, subject to the type of information desired to be represented. These techniques employ various means for collecting and manipulating nuclear magnetic resonance data for the generation of images. Such methods are described in the literature available in the art and include, without limitation, Fourier imaging, planar imaging, echo planar imaging, projection-reconstruction imaging, spin-warp Fourier imaging, gradient recalled acquisition in the steady state (GRASS) imaging also known as fast low angle shot (FLASH) imaging, and hybrid imaging.

Such imaging methods are described in, for example, Ernst et al., *Principles of Nuclear Magnetic Resonance in One and Two Dimensions* (1987) (Reference 52), particularly Chapter 10, "Nuclear Magnetic Resonance Imaging", pages 539–564; Shaw, D. D., "The Fundamental Principles of Nuclear Magnetic Resonance", Chapter 1 in *Biomedical Magnetic Resonance Imaging*, S. W. Wehrli et al. eds. (1988) (Reference 53); and Stark et al. eds., *Magnetic Resonance Imaging*, Vol. 1, 2d ed. (1992) (Reference 40). These publications are incorporated herein by reference.

The selection of imaging method will depend on the behavior of the noble gas nucleus under investigation, the nature of the sample and the degree of interaction of the nucleus with the sample. The selection of imaging method will also depend on whether one or more spatial dimensions of the spatial distribution of the noble gas is desired to be represented and whether a temporal or time-dependent dimension is desired to be represented. When a multidimensional representation is desired such representation may be generated by, for example, multi-slice imaging or volume imaging.

It is generally preferred that the image or representation be generated by a method which is as fast and as sensitive as possible. Preferred imaging methods include the FLASH or GRASS imaging method and the echo-planar imaging (EPI) method. These methods are preferred for their capacity to generate images through fast data acquisition, thereby conserving polarization of the noble gas. EPI is especially preferred because it is a relatively fast method and requires only one radio-frequency (RF) pulse per image. It thus permits maximum utilization of the available polarization. These preferred methods also permit fast time resolution of time-dependent phenomena in human and animal subjects. Such applications include, for example, magnetic resonance angiography (MRA) studies, functional imaging of the nervous system (e.g., brain), as well as studies of variations in cardiopulmonary and circulatory physiological states.

The nuclear magnetic resonance imaging method of the invention also includes the registration of multiple imaging modalities. For example, using coils tunable to $^{129}Xe$ frequencies and the frequencies of one or more other magnetic probes permits enhanced data interpretation. Such combined multiple imaging approaches would include, for example the combined imaging of $^{129}Xe$ with $^1H$, and the imaging of more than one noble gas, such as imaging of $^{129}Xe$ with $^3He$. In this embodiment, geometric image registry and overlay are possible, including the generation of false-color images, in which distinct colors would represent distinct probes. Image subtraction techniques would also be possible using combinations of $^{129}Xe$ with other probes, or combinations of noble gas probes.

The noble gas being imaged is preferably distributed spatially in at least one physical phase such as a gas, liquid, gel, or solid. The noble gas may be imaged as distributed in two or more physical phases in one sample. The noble gas being imaged may be distributed on a solid surface. The noble gas may be imaged in association with various materials or environments such as, without limitation, zeolites, xenon clathrates, xenon hydrates, and polymers.

The sample being imaged using a noble gas may include an in vitro chemical, in vitro biological or in vivo biological, system. When the noble gas distribution in an in vivo biological system is imaged, the system may include one or more human or animal subjects. The noble gas is preferably distributed in an organ or body system of the human or animal subject, including, without limitation, lung tissue, nervous tissue, brain tissue, gastrointestinal tissue or cardiovascular tissue or combinations thereof. Alternatively, the noble gas may be distributed in an anatomical space such as, without limitation, lung space, gastrointestinal tract space, peritoneal space, bladder space or combinations thereof.

The noble gas may be contacted with the sample to be imaged in gaseous or liquid form, either alone or in combination with other components in a gaseous or liquid composition. The noble gas may be combined with other noble gases and/or other inert or active components. The noble gas may be delivered as one or more boluses or by continuous or quasi-continuous delivery.

In a preferred embodiment, there is also provided a method of performing nuclear magnetic resonance imaging of an animal or human subject by administering an imageable amount of a hyperpolarized noble gas to the subject, employing an NMR spectrometer to generate and detect radio-frequency signals derived from the magnetic resonance of the noble gas, processing the detected signals to obtain an NMR parameter data set as a function of the spatial distribution of the noble gas, and further processing the data set to generate a representation corresponding to at least one dimension of the spatial distribution of the noble gas.

The noble gas may be administered to a human or animal subject as a gas or as a liquid, either alone or in combination with other noble gases and/or other inert or active components. The noble gas may be administered as a gas by either passive or active inhalation or by direct injection into an anatomical space such as lung or gastrointestinal tract. The noble gas may be administered as a liquid by enteral or parenteral injection. The preferred method of parenteral administration includes intravenous administration, optionally by contacting blood with the noble gas extracorporeally and reintroducing the noble gas-contacted blood by intravenous means.

The cost of a purified noble gas tends to be relatively high as compared to the cost of common gases such as nitrogen or carbon dioxide. The cost is especially high in the case of Xenon which has been enriched to, for example, 70% $^{129}Xe$. However, being inert, the noble gas is not metabolized in biological systems and can be recovered. For example, Xenon can be recovered from the exhaled breath of human subjects over about a 20 minute period. Such apparatus for noble gas recovery and repurification would include, for example, a cold trap and/or a zirconium getter apparatus, such as are known in the art. Other apparatus for recovery of noble gases may be employed.

It is preferred that, because of the high cost of the noble gas, the gas be maintained in a system which is substantially sealed to prevent loss to the atmosphere. Sealed containment apparatus would include a noble gas source, such as a gas canister or compressed gas tank, conduits to and away from a sample, as well as recovery apparatus.

The noble gas source may include a permanent or semi-permanent canister or pressurized containment apparatus. Alternatively, the noble gas may be supplied in disposable or refillable one-use containers such as pressurized gas ampoules or cylinders. The noble gas source may be integrated with a sealed noble gas supply and recovery system or may be stored separately and affixed to and opened to the supply and recovery system on a periodic or as-needed basis.

The sample to be studied, whether a physical structure, a chemical system, an in vitro system, a living animal or human host, or other suitable sample, is preferably imaged using apparatus which substantially prevents loss of Xenon to the environment, although the invention may be practiced without such apparatus. Thus, a sample may be imaged while maintained in a sample chamber substantially suffused or suffusable with the noble gas. Alternatively, for human or animal subjects, the subject may be fitted with an administration device, such as a sealed mask, for administration of the noble gas. In such cases, the sample chamber or noble gas administration device preferably communicates with a noble gas source and/or a noble gas recovery apparatus.

A hyperpolarized noble gas may be stored for extended periods of time in a hyperpolarized state. Storage systems capable of cryogenic storage of a hyperpolarized noble gas are preferably able to maintain temperatures such that noble gas is stored in frozen state. Frozen $^{129}$Xe can be reasonably maintained at fields of $\geq 500$ Gauss at temperatures ranging from 4.2K (liquid helium temperature), for which $T_1$ is about a million seconds (10 days), to 77K (liquid nitrogen temperature), for which $T_1$ is about 10 thousand seconds. The fields necessary here may be provided by a small permanent magnet or by a larger electromagnet typically carrying on the order of ten or more amperes of current. For $^3$He, things are quite different. Relaxation rates are such that low 10–20 Gauss fields can be used to hold it at room temperature-a few atmospheres will live for days under these conditions. The field here could also be a permanent magnet or a Helmholtz pair of coils carrying about one ampere of current. The conditions required for maintaining other hyperpolarized noble gases may be determined by those skilled in the art.

A noble gas which has been hyperpolarized by spin exchange with an alkali metal may be stored either before or after removal of any alkali metal used in spin exchange hyperpolarization techniques. In all cases in which rubidium or other alkali metal would interfere with the behavior of the system the alkali metal is removed before introduction of the noble gas to the sample. This removal of toxic alkali metal is important in biological samples and is especially critical in cases in which the sample is a living human or animal subject.

An alkali metal removal device may be employed either distant from the imaging site or proximally thereto. For example, the alkali metal removal device may be incorporated in a sealed noble gas administration system at a point prior to a conduit to a sample chamber or other administration device.

An alkali metal removal device would generally include a conduit for conducting the noble gas to a region or chamber which is cooler than the pumping region. At room temperature, the saturated vapor pressure of Rubidium, i.e., the pressure in an enclosure in the presence of a pool of liquid Rubidium, is about $10^{-9}$ atm. By moving the noble gas away from any macroscopic pools of liquid Rubidium, any remaining vapor is likely to plate out onto a cool (e.g., room temperature) surface, thereby never reaching an experimental subject. It is preferred, however, that a cold trap, such as is known in the art, be used.

The delivery of the noble gas to a sample may be performed as single or multiple bolus delivery. Such delivery would ordinarily be suited to the study of systems in which observations of the change in noble gas distribution is important. Such systems would include, inter alia, human or animal subjects in which an anatomical or physiological event or events are being examined as a function of time. Alternatively, the delivery of the noble gas to a sample may be performed as a continuous or quasi-continuous delivery. Such delivery would ordinarily be desired when steady state analyses of samples are desired. For example, high resolution imaging of human or animal organ systems would be possible by sequential imaging of steady state Xenon concentrations by data processing, e.g., image subtraction or signal averaging. Hyperpolarized Xenon or other noble gas could also be used as a marker or for contrast enhancement in whole body $^1$H$_2$O NMR imaging in which the noble gas NMR signal could be digitally subtracted from the $^1$H$_2$O NMR image. For example, hyperpolarized Xenon could be introduced in the gastrointestinal tract of a subject to inflate the regions therein and to provide contrast enhancement when digital subtraction of signals is performed.

Comparative data have been obtained which illustrate the NMR behavior of $^{129}$Xe in various environments. For example, various groups have determined chemical shift and relaxation rates ($T_1$ and $T_2$) for $^{129}$Xe in environments such as n-octanol, benzene, water and myoglobin. (See References 2, 16). Octanol represents a relatively non-polar lipid-like environment resembling the interior of the cell membrane, water models aqueous regions, and the myoglobin solution represents a protein to which Xenon is known to bind. (Reference 54). The measured range of resonance frequencies for Xenon extends approximately 300 ppm over the gas and condensed phase. (Reference 2). Although the range of chemical shifts observed in these model biological systems is not as large as that in other solvents, it is large compared to the relevant $^{19}$F brain resonance values that have been reported. (Reference 3).

Moreover, the huge range of $T_1$ values is extraordinary. Table III lists some reported values of $T_1$ and $T_2$ for $^{129}$Xe in octanol, water and aqueous Fe(III) metmyoglobin (Reference 54); models representing two major cell compartments, lipid membrane and cytosol. The values for $T_1$ in octanol, 80 s, and water, 130 s, provide an indication of the extraordinarily long lifetimes of $^{129}$Xe polarization (anoxic tissue with no other relaxers). In other biological environments, longer $T_1$ values are possible. The lower limit is unknown: The 5 ms $T_1$ in 10% Fe(III) metMb (a strong relaxer) implies a physiological lower limit much higher than this. The extremely short $T_1$ and $T_2$ values found for the protein solution certainly occur because Xenon binds very near the paramagnetic center of metmyoglobin. (Reference 54).

TABLE III

| ENVIRONMENT | $T_1(s)$ | $T_2(s)$ | $\Delta^{129}Xe$ (ppm)* |
|---|---|---|---|
| Octanol | 78.5 | 5.3 | 204.6 |
| Water | 131.3 | 5.3 | 195.3 |
| Myoglobin | $5.2 \times 10^{-3}$ | $0.57 \times 10^{-3}$ | 199.4 |
| Benzene | 160.5 | 0.88 | 196.4 |
| Pure Gas Phase (1 atm) | 56 hrs | $\leq$56 hrs | 0.4 |

*Shift relative to shift observed in pure gas at 0 atm.

The value of $T_1$ in benzene at 300° K., i.e., $T_1=160$ s, agrees well with that of Diehl and Jokisaari, i.e., $T_1=155.0$ ±6.2 s, at 9.4 T and 300° K., (Reference 43), rather than with the value of $T_1=240$ s obtained by Moschos and Reisse. (Reference 55). Measurements of $T_1$ and $T_2$ for $^{129}Xe$ are difficult to obtain, hence scarce. The values quoted here represent a significant fraction of the known list. The difficulties are obvious: typically, longitudinal relaxation times are long; low signal strength requires signal averaging of many free induction decay (FID) traces, hence very long overall accumulation times. The problem is particularly acute in aqueous systems: as noted above, the solubility of Xenon at 30° C., 0.5 atm. is 48 mM in octanol, but only 2.4 mM in water.

It would be desirable to investigate the possibility of observing multiple $^{129}Xe$ resonances within brain tissue, but the small signal from the small, largely aqueous brain volume of a live mouse, breathing an atmosphere of 50–70% normal Boltzmann-polarization $^{129}Xe$, would require an enormous time interval of data collection for adequate signal averaging.

Seeking a system that would be tolerably stable for the necessary time interval, capable of being sealed with Xenon at 2–3 atm, but close enough to functioning brain cells, the behavior of Xenon in a synaptosome suspension has been studied. (Reference 16). Synaptosomes are presynaptic nerve terminals sheared away from their attachments to form resealed subcellular pseudocells that retain the morphology and chemical composition of the terminal nerve cell region, and much of the membrane functionality. Synaptosomes are rich in postsynaptic adhesions and constitute a source for postsynaptic membranes, synaptosomal mitochondria, transmitter receptors, and cleft material.

FIG. 1a shows a smooth, high S/N spectrum of 3 atm Xenon in equilibrium over a 10% (wet weight) rat brain synaptosome suspension as described by Albert et al. (Reference 16). This spectrum is resolution-enhanced with Gaussian broadening of 0.01 Hz and line broadening of −5.0 Hz. Two peaks can be seen; a broad resonance of about 3.4 ppm to higher frequency of a narrow component. The narrow peak appeared 0.33 ppm to higher frequency of that of $^{129}Xe$ in pure water, and is likely due to bulk magnetic susceptibility shift effects. Although collected using a simple one-pulse sequence, the spectrum required 27 hours of signal averaging to obtain the degree of signal strength and resolution shown.

An alternative model for investigating $^{129}Xe$ behavior in brain tissue has also been tested. FIG. 1b shows a $^{129}Xe$ spectrum obtained from a sample of rat brain homogenate as described by Albert et al. (See Reference 16). This spectrum also shows two resolved peaks; indicating that slow-exchange compartmentalization of $^{129}Xe$ in complex biological systems can also be observed. The decrease in high-field signal (aqueous $^{129}Xe$) as compared to the synaptosomal spectrum (FIG. 1a) reflects a decrease in water content in the preparation. The spectrum of FIG. 1b required 8 hours of data accumulation, reflecting the difficulties inherent in attempting to examine $^{129}Xe$ in biological systems.

The behavior of $^{129}Xe$ in brain tissue has been studied by investigating whether any signal could be obtained from $^{129}Xe$ in whole rat brains. (See Reference 16). FIG. 1c shows a spectrum of $^{129}Xe$ obtained from a whole rat brain preparation, again showing two resolved peaks, but obtained with further decreased S/N. The two resolved peaks provide further evidence that $^{129}Xe$ is slow-exchange compartmentalized in complex biological systems. A further decrease in the proportion of high-field signal (aqueous $^{129}Xe$) as compared to FIGS. 1a and 1b, reflects a further decrease in water content in this sample preparation. The spectrum required 8 hours of data accumulation, again illustrating the difficulty of obtaining NMR data from $^{129}Xe$ in biological systems.

It is known that $^{129}Xe$, which has a long longitudinal relaxation time in the gas phase, can be relaxed by magnetic dipole-dipole interaction and/or Fermi-Contact interaction with the unpaired electron spins of dioxygen. (Reference 18). The solubility of Xenon (and also of dioxygen) in water is low. Due to the low sensitivity of the $^{129}Xe$ signal, the time required for determining the relaxivity of $O_2$ toward $^{129}Xe$ with a series of $T_1$ determinations over a range of $O_2$ concentrations in water would be prohibitively long.

The relaxivity of $O_2$ toward $^{129}Xe$ has been measured in only one liquid, i.e., octanol, which models an amphipathic membrane lipid. (Reference 17). The observed relaxivity, 0.029 $sm^{-1}mM^{-1}$, is about three times larger than that estimated from previous reports for gas-phase relaxation, i.e., (Reference 18), 0.0087 $s^{-1}mM^{-1}$ as might be expected for encounters in the condensed phase. The dioxygen relaxivity for $^{129}Xe$ is constant over the concentration range studied, and thus $1/T_1$ will be a linear function of $O_2$ concentration over the entire physiological range (0–0.2 atm, 0–0.2 mM). This translates into a $T_1$ value of 18 s in air-saturated lipid, and 80 s in anaerobic lipid, in the absence of other relaxers. This is the first reported value for the $O_2$ relaxivity toward $^{129}Xe$ in a condensed phase. $T_2$ values over these $O_2$ concentrations have been determined to range from 0.5 to 5.0 s. These results indicate that the range of $T_1$ to be expected in tissue in vivo is about 1–20 s. In fact, given the relative inefficiency of the known non-paramagnetic relaxation mechanisms, it is suspected that $T_1$ in many tissues will not fall below seconds or even tens of seconds. These results are of critical importance to physiological studies using $^{129}Xe$ magnetic resonance spectroscopy.

Using Boltzmann polarization $^{129}Xe$, data have been obtained which allow estimation of $T_1=38$ s (±8 s, SD) for $^{129}Xe$ dissolved in rat blood at 293° K. (Reference 17). However, since 12 hours were required to obtain this data set, the result serves only to estimate what the normal physiological $T_1$ might be in vivo.

This estimate of $T_1 \approx 38$ s for $^{129}Xe$ dissolved in rat blood at 293° K. is very encouraging. Although this result, obtained over a 12 hr period (using Boltzmann $^{129}Xe$), might not be representative of physiological blood, the changes likely to occur in blood maintained at room temperature for long periods, e.g., methemoglobin formation, would tend to decrease the value observed for $T_1$. One can also estimate $T_1$ values for other model systems. The $T_1$ of $^{129}Xe$ in water has been measured at 300° K. to be 130 s. (Reference 16). $^{129}Xe$ exchange with protein binding sites will lower this value, (Reference 16), but the contribution from aqueous $O_2$ should be minimal. $T_1$ for $^{129}Xe$ in octanol, a classic membrane phase model, is 80 s. (References 16–17). Since membrane bilayers sequester both Xe and $O_2$, it should be possible to use the values for Xenon and Oxygen distribution ratios, (Reference 45), between octanol and water of 20:1 and 6:1, respectively, and of the $O_2$ relaxivity in octanol of 0.029 $s^{-1}mM^{-1}$ at 300° K., (Reference 17), to estimate the $T_1$ value for $^{129}Xe$ in fully oxygenated membranes to be >15 s. While the actual values of $T_1$ in each tissue must be, and remain to be, determined, it is expected that the minimum value will fall above 15 s, a duration sufficient to enable significant accumulation of polarized $^{129}Xe$ in major tissues.

The unusual and extraordinary properties of hyperpolarized noble gases permit imaging of a wide variety of organs, body systems, and anatomical structures. Such structures can be imaged in live or deceased subjects, depending on application, and such subjects can include human as well as animal subjects. For example, hyperpolarized Xenon will have particular clinical importance in providing nuclear magnetic resonance imaging of neural tissue diseases, vascular plaques, compromised blood flow, tumors, as well as functional imaging of the brain's response to sensory stimuli. The properties of other noble gases will render them useful in a variety of other situations. For example, it is expected that because of its low solubility, $^3He$ will be of major clinical importance in imaging anatomical spaces such as lung or other artificially inflated organs.

The differential solubility of Xenon and other lipid soluble, hyperpolarizable noble gas isotopes would permit noble gas NMR differentiation between white and gray matter in brain tissue, while lipid membranes are essentially invisible to $^1H_2O$ MRI. For example, with respect to neural tissue disease, in white matter regions of the lower medulla and the spinal cord $^1H_2O$ MRI contrast is poor, while the high lipid solubility of Xenon and other noble gas anesthetics will permit imaging of hyperpolarized isotopes. Such imaging would have diagnostic importance for patients suffering from nerve tissue demyelination. Hyperpolarized noble gas MRI would be of use for imaging of subdural hematomas as well as cystic and necrotic changes. Indications of low noble gas uptake in avascular regions would be valuable in demonstrating isodense fluid collections. (Reference 56). With respect to differentiation between tumors and infarcts, in ischemic lesions, noble gas washin/washout is delayed and blood flow is diminished, while in infarcted tissue, only the noble gas equilibrium level is diminished. In cases of multiple sclerosis, $^1H_2O$ MRI often cannot provide useful images of plaques, while differential noble gas uptake (high in normal tissue vs. low in demyelinated plaques) would permit effective Xenon images. Similarly, in cerebral vascular and peripheral blood vessel plaques, the plaques have little or no noble gas uptake and would appear dark in a noble gas image. (Reference 57).

Images of Xenon (and other noble gas anesthetics) would also indicate cerebral, coronary and peripheral vessel defects; providing obvious indications of blood vessel constrictions and aneurysms. In particular, measurements of regional cerebral blood flow would be possible with greater exactness than is possible with other techniques. Also, study of the effects of spasms on blood flow in cases of subarachnoid hemorrhage would be rendered possible.

Functional study of brain tissue is also expected to be dramatically enhanced by the imaging of hyperpolarized noble gas anesthetics, especially Xenon, according to the invention. For example, changes in local blood flow caused by visual, tactile, and other stimuli should produce dramatic fluctuations in $^{129}Xe$ signal intensity. In addition, the elucidation of the precise relationships between neurological changes and psychological states has been a major goal of neurobiologists. Electroencephalography, positron emission tomography (PET), and recently, $^1H_2O$ MRI, have been used in this field. Hyperpolarized Xenon MRI, with its high sensitivity, as exploited through fast electronics, has the potential to make huge contributions to this area. Disease states such as epilepsy, schizophrenia, depression and bipolar illness can be studied.

Clearly, hyperpolarized noble gas MRI has essentially unlimited potential application in medical settings. Hyperpolarized noble gas MRI could displace or supplement conventional MRI, and even the ubiquitous but intrusive X-ray CT scan, in at least several large areas: (1) the lung, heart, and cardiovascular systems; (2) the brain, especially since brain membrane lipids are invisible using current techniques; (3) brain function, since the $^{29}Xe$ signal will respond directly and strongly to metabolic changes in neural tissue.

Noble gas MRI promises to complement $^1H_2O$-based imaging in a dramatic way. The near million-fold enhancement in sensitivity to noble gases enabled by hyperpolarization should result in temporal and spatial resolution in imaging superior to that achievable with $^1H_2O$. In addition, the solubility of, for example, Xenon in lipids should permit imaging of organs that currently require far more intrusive techniques such as X-ray computerized tomography scanning.

The following non-limiting Examples are intended to further illustrate the present invention. In the Examples provided below, the experimental conditions were as follows unless otherwise noted: magnetic resonance spectra were obtained using a Bruker MSL 400 spectrometer equipped with a 9.4 T widebore vertical magnet, an ASPECT 3000 computer, a BVT 1000 variable temperature control unit, and employing a high-gradient Bruker micro-imaging probe and solenoidal transceiver coils of 13.3 and 20 mm diameter, operating at 110.7 MHz for $^{129}Xe$ and 400 MHz for $^1H$. The spectrometer was not field frequency locked during the image acquisitions.

EXAMPLE 1

Xenon-Oxygen and Xenon-Oxygen-octanol "Boltzmann" imaging phantoms were prepared by standard quantitative high-vacuum gas-transfer techniques. Xenon gas, enriched to 70% $^{129}Xe$, was obtained from Isotec Inc., of Miamisburg, Ohio.

Image acquisition made use of a Fast-Low-Angle-SHot (FLASH) phase refocused, free-precession, fast gradient-echo imaging sequence as described by Haase et al. (Reference 58). This sampling-pulse technique was originally introduced by Look et al. (Reference 59). Standard proton microimaging gradients of 100 mT/m yielded a 50×50 $mm^2$ field of view for $^{129}Xe$. A 128×64 encoding matrix was used, which set the spatial resolution to 0.8× 0.8×8 $mm^3$.

Figure 2A:
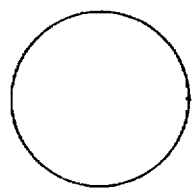
FIG. 2a shows a graphical representation of a glass sphere 20 mm in diameter.
Figure 2B:
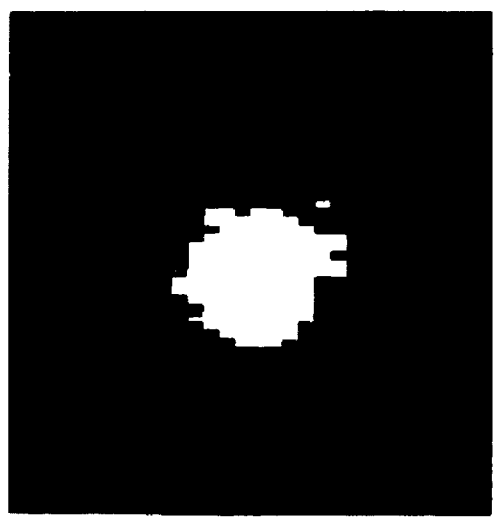
FIG. 2b shows a nuclear magnetic resonance image of Boltzmann polarized $^{129}$Xe gas in a 20 mm diameter glass sphere.
Figure 3A:
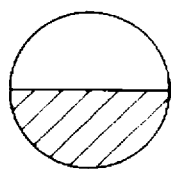
FIG. 3a shows a graphical representation of a glass sphere, 20 mm in diameter, containing octanol (shaded region) and Xenon gas (unshaded region)
Figure 3B:
FIG. 3b shows a nuclear magnetic resonance spectrum illustrating NMR signals obtained from $^{129}$Xe in gas phase and in octanol.
Figure 3C:
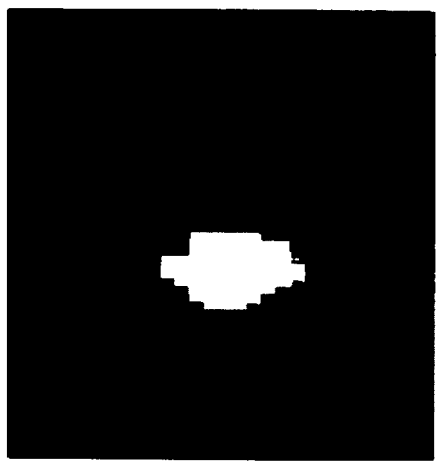
FIG. 3c shows a nuclear magnetic resonance image of $^{129}$Xe in octanol in 20 mm glass sphere.
Figure 3D:
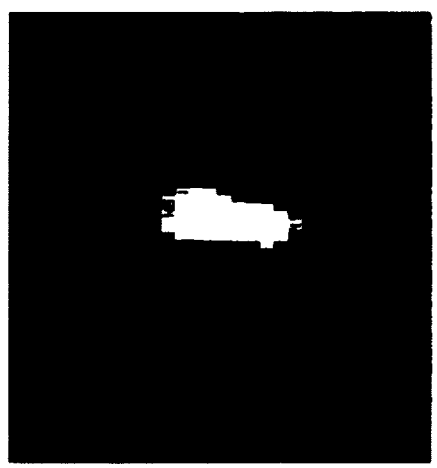
FIG. 3d shows a nuclear magnetic resonance image of $^{129}$Xe in gas phase in a 20 mm glass sphere.
Figure 4A:
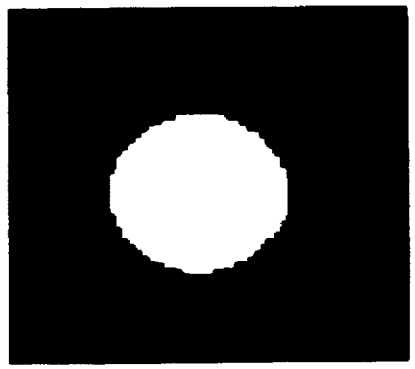
FIG. 4 shows a series of nuclear magnetic resonance images of a hyperpolarized $^{129}$Xe gas phantom, representing different mutually parallel planes.
Figure 4B:
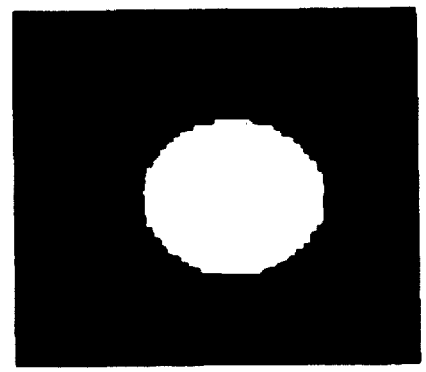
Figure 4C:
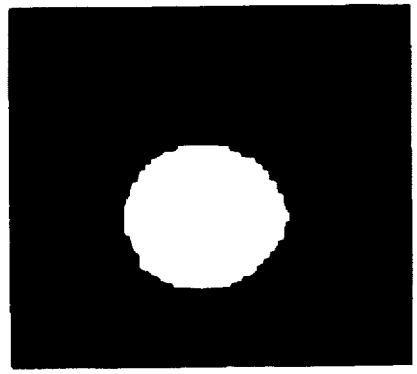
Figure 4D:
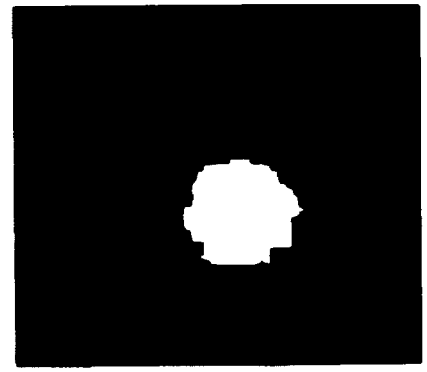

FIG. 2b illustrates an image of a 20 mm $^{129}Xe$ glass phantom containing 5 atm Xe at Boltzmann equilibrium polarization (2 atm $O_2$ was used to reduce $T_1$). This image may be compared to those images in FIG. 3c and 3d. FIG. 3 illustrates the spectrum and images of a $^{129}Xe$ gas-octanol glass phantom containing ca. 5 atm Xe at Boltzmann equilibrium polarization (2 atm $O_2$ was used to reduce $T_1$). The observed resolution of 1×2×20 $mm^3$ per volumetric picture element (voxel) was achieved by accumulating 64 replicate FLASH imaging sequences over 7 min. Note that, as shown in FIG. 3b, the $^{129}Xe$ signals from the gas and octanol phases are separated by 186 ppm: this implies that the imaging gradients produce no overlap.

EXAMPLE 2

Images of hyperpolarized $^{129}$Xe in glass sphere phantoms were obtained as follows. Optical pumping cells were constructed of 13–18 mm diameter Pyrex® spheres. Before filling, the cells were coated with a siliconizing agent Surfasil obtained from Pierce, of Rockford, Ill., attached to a high vacuum manifold, evacuated to ~$10^{-8}$ Torr, and baked at 150° C. for about 24 hours. The silicone coating apparently reduces relaxation of $^{129}$Xe on the walls of the glass sphere, permitting creation of larger polarizations. The spheres were then filled with 400–1800 Torr Xe, 75 Torr $N_2$ and a few milligrams of Rubidium metal. Once filled with the test gas or gas/liquid, the glass cells were flame sealed.

Optical polarization was performed generally in accordance with techniques known in the art, in particular the methods of Cates et al., (Reference 35), as follows. The cells were heated to 85° C. The entire volume of the cell was exposed to 2–4 W of 795 nm Rb $D_1$ laser light from a Spectra Physics 3900S Titanium-Sapphire laser, which was itself pumped by a Spectra Physics 171 Argon-Ion laser operating at 18–23 W. Both lasers were obtained from Spectra Physics of Mountain View, Calif. The laser illumination of the cells was performed in the bore of the 9.4 T magnet described above, at a field strength of 9.4 T. After 15–20 min. of optical pumping, the cells were cooled to room temperature and employed for MR experiments.

Image acquisition made use of a Fast-Low-Angle-SHot (FLASH) phase refocused, free-precession, fast gradient-echo imaging sequence as described by Haase et al. (Reference 49). This sampling-pulse technique was originally introduced by Look et al. (Reference 50). This technique takes advantage of the fact that, for small θ, the transverse projection, i.e., sin θ, allows substantial signal strength, while the loss in longitudinal projection, i.e., 1-cos θ, permits only a small loss in Z-magnetization per pulse. Standard proton microimaging gradients of 100 mT/m yielded a 50×50 mm$^2$ field of view for $^{129}$Xe. A 128×128 encoding matrix was used, which set the spatial resolution to 0.37×0.37×1 mm$^3$.

FIG. 4 illustrates a series of images obtained from slices in the plane defined by the Y and Z axes through a 13 mm diameter cell containing 400 Torr of laser-polarized Xenon. The laser-polarization was performed within the bore of the 9.4 T magnet. Each image was collected in a single FLASH sequence lasting 600 msec., with 0.37×0.37×1 mm$^3$ resolution. FIG. 4d displays the variation in $^{129}$Xe intensity characteristic of an image slice through a domed end of the sphere. The other slices were obtained from sections closer to the center of the spherical phantom and are more homogeneous and uniformly bright. For this experiment the $^{129}$Xe polarization was estimated to be 25–30% by signal comparison to a cell of identical dimensions containing Xenon at a higher pressure but at Boltzmann polarization (illustrated in FIG. 3b).

EXAMPLE 3

Nuclear magnetic resonance images of mouse lungs were obtained using hyperpolarized $^{129}$Xe according to the following method.

In order to deliver a quantity of hyperpolarized $^{129}$Xe to a biological specimen, several obstacles must be overcome. To date, $^{129}$Xe has only been successfully hyperpolarized in very pristine environments such as sealed glass cells. Such purity is essential because any paramagnetic impurities will greatly reduce the longitudinal relaxation time $T_1$ of the gas and thus lower the achievable polarizations. To preserve the successful sealed-cell polarization techniques and still deliver the polarized gas to an external specimen, cells equipped with thin break seals were developed. A glass delivery tube, equipped with a piston, was devised so that, once the $^{129}$Xe was polarized, the cells could be sealed into the delivery tube, their break seals broken by the action of the piston, and the polarized gas freed to expand into the biological specimen.

Figure 7:
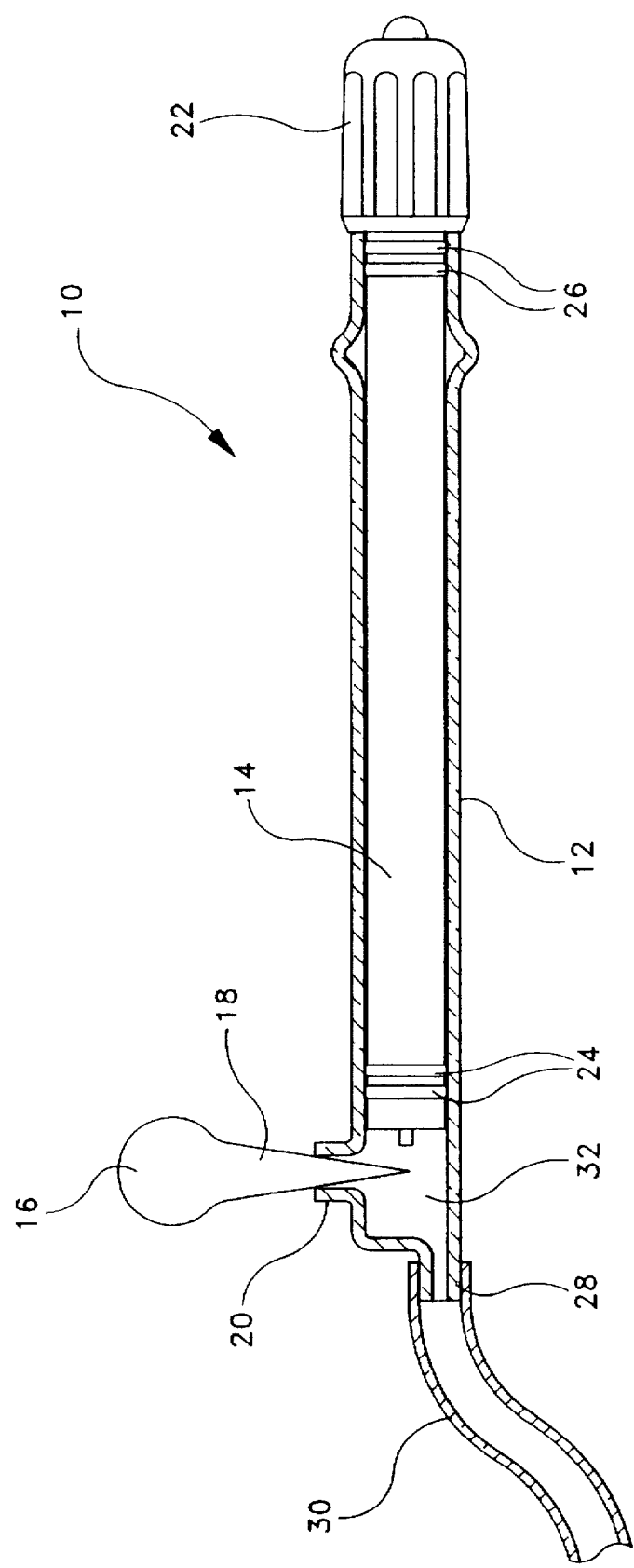
FIG. 7 shows a longitudinal section view of a noble gas delivery device for nuclear magnetic resonance imaging of noble gases.

FIG. 7 shows a delivery tube device 10 developed for the delivery of a noble gas, e.g., $^{129}$Xe, from a sealed cell 16 to a sample within the bore of an NMR spectrometer. The delivery device 10 includes a cylinder 12 within which a piston 14 can be controllably displaced in an axial direction. The cylinder 12 is threaded on an external surface at one end. The cylinder threads match threads on the internal surface of a control handle 22 which is rotatably attached to the piston 14. The device also includes at least one O-ring 24, 26 providing a gas tight seal between the internal surface of the piston 14, while permitting axial movement of the piston relative to the cylinder. At the other end of the cylinder 12, i.e., opposite the threads adapted for receiving the control handle 22, is sealable inlet port 20 adapted for receiving a breakable neck 18 of the sealed cell 16 containing pressurized noble gas. The inlet port 20 is sealed with a glass-sealing wax around the breakable neck 18 of the sealed cell 16 containing pressurized noble gas. The delivery device 10 also includes an outlet 28 communicating with the inlet port 20 connected to a conduit 30 to a medical sample and through which a noble gas can be delivered to the sample. The dead volume 32 in the delivery device is preferably as small as possible to minimize dilution of the noble gas as it passes from the cell 16 to the medical sample during operation of the delivery device 10. The O-rings 24 are therefore also preferably positioned as close to the break point of the sealed neck 18 as possible.

The device 10 is preferably operated in situ, i.e., inside the NMR spectrometer used for imaging the noble gas in the sample, and is designed so that the seal of cell 16 can be broken by remote manipulation of the control handle 22, which when rotated displaces the piston 14 toward the neck 16 until contact with neck 16 is made sufficient to break neck 16 and release the pressurized noble gas. Mouse lungs, intact with trachea and heart were freshly excised from 30–35 g Swiss-Webster mice which had been freshly euthanized with 100 mg/kg sodium pentobarbital. The trachea was intubated with 1 mm OD Silastic medical grade tubing and the heart-lung preparation was placed in a 10 mm internal diameter glass cylinder, inserted into a 13.3 mm imaging coil and flushed with one inflation of $N_2$. Polarized Xenon gas was prepared as described in Example 2 except that the cells were illuminated away the bore of the 9.4 T magnet at a low field strength (approximately 10 mT). The hyperpolarized $^{129}$Xe was delivered through the use of 18 mm OD Pyrex spheres provided with break-seal stems which had been sealed into a vacuum tight glass delivery tube (illustrated in FIG. 7) suspended in the bore of the magnet. The tubing from the mouse trachea was attached to the end of the delivery tube. Once the break-seal had been fractured, the 13–20 atm/cm$^3$ Xenon was free to expand into the lung. Gas pressures and volumes were adjusted to inflate the lung to approximately 1 atm of gas within one second, during which time only a minimal amount of relaxation of the polarization could take place.

Images were obtained using the NMR protocol described in Example 2 above. FIG. 5 presents a sequence of images illustrating the time-evolution (t=0–10 s) of the distribution of hyperpolarized $^{129}$Xe entering the lung of a heart preparation. The images represent 1.0 mm thick slices through mouse lung inflated with laser-polarized $^{129}$Xe gas. The plane of the slices is perpendicular to the (absent) vertebral column (i.e., anatomical cross section). Voxel size is 0.37× 0.37×1 mm$^3$, and specimen diameter is 10 mm.

Figure 5A:
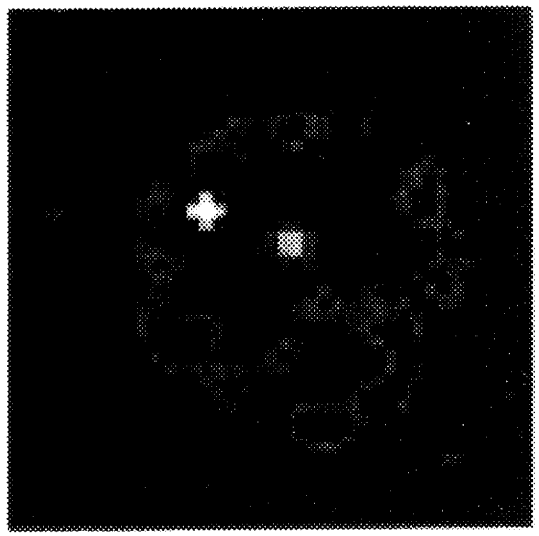
FIGS. 5a–5c show a sequence of nuclear magnetic resonance images of a mouse lung inflated with hyperpolarized $^{129}$Xe gas.

FIG. 5a shows a $^{129}$Xe image of lung obtained immediately after inflation (i.e., t=0 s), such that the lung is completely expanded to fill the glass cylindrical enclosure. At this point, the lung still largely contains the N$_2$ from the dead volume of the delivery system. Only the trachea, hints of the bronchi, and some of the lung periphery have received $^{129}$Xe at this point.

Figure 5B:
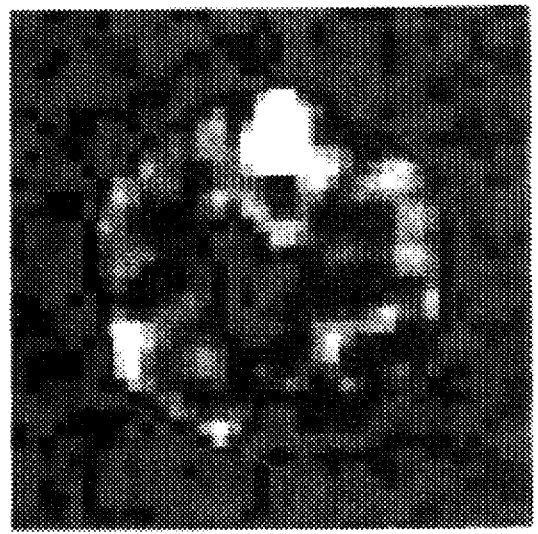

FIG. 5b is an image obtained about 1 s later than the image in FIG. 5a (i.e., t=1 s). At this time the maximally inflated lung has received substantial $^{129}$Xe. Both lobes of the lung can be seen with significant contrast variation and a small darker central region where the heart excludes the Xenon gas. Note that the lobes of the lung have expanded to press against the interior surface of the 10 mm diameter glass tube in which they are contained.

Figure 5C:
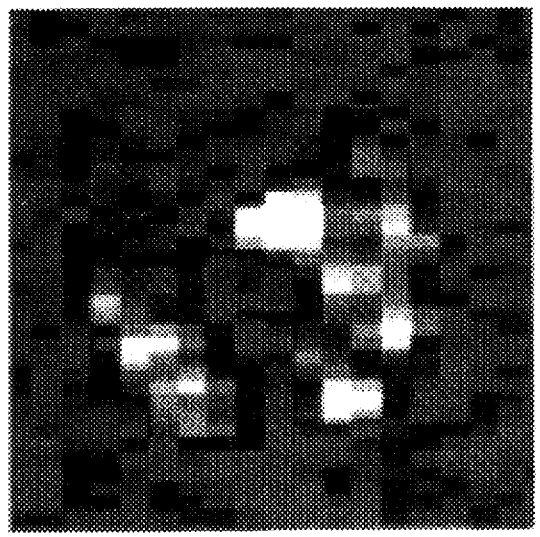

FIG. 5c is an image obtained seven seconds later than the image obtained in FIG. 5b, (i.e., t=8 s), showing that the lung has partially deflated. The lobes are more clearly delineated and the central heart space is more apparent. The y-axis resolution of this image is lower because it was anticipated, incorrectly, that the $^{129}$Xe magnetization remaining after the image in FIG. 5b would necessitate the use of larger voxels and fewer slice selection pulses. Thus not all imaging parameters were optimized in acquiring these images. Optimization would likely have produce resolution between 2 and 4 times better than that achieved.

Figure 5D:
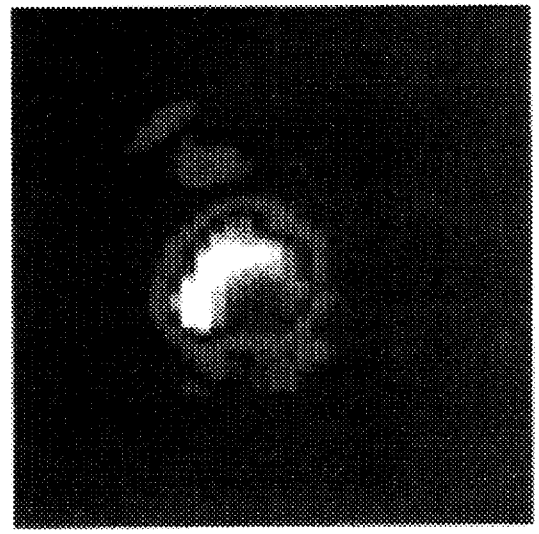
FIG. 5d shows a nuclear magnetic resonance image of $^1$H in a mouse heart.

Finally, FIG. 5d shows a $^1$H image of the same slice of the heart-lung preparation. The heart, just below center, is the primary source of intensity, while a drop of saline delineates the upper left boundary, as confirmed by visual observation of the sample.

Thus, the $^{129}$Xe lung image is an excellent complement to standard proton NMR imaging. The $^{129}$Xe image is clearly bright where the $^1$H image is dark, and vice versa. Lung tissue is not readily seen in water proton images; only at magnified intensity does one see a faint trace of the lobes. It is believed that this phenomenon is not the result of a relative lack of protons, but is almost certainly due to the extreme local variation in bulk magnetic susceptibility at the highly complex gas-tissue interface which causes extremely short T$_2$ values. (See Reference 8). This is, evidently, not a problem for gas phase $^{129}$Xe.

Figure 6:
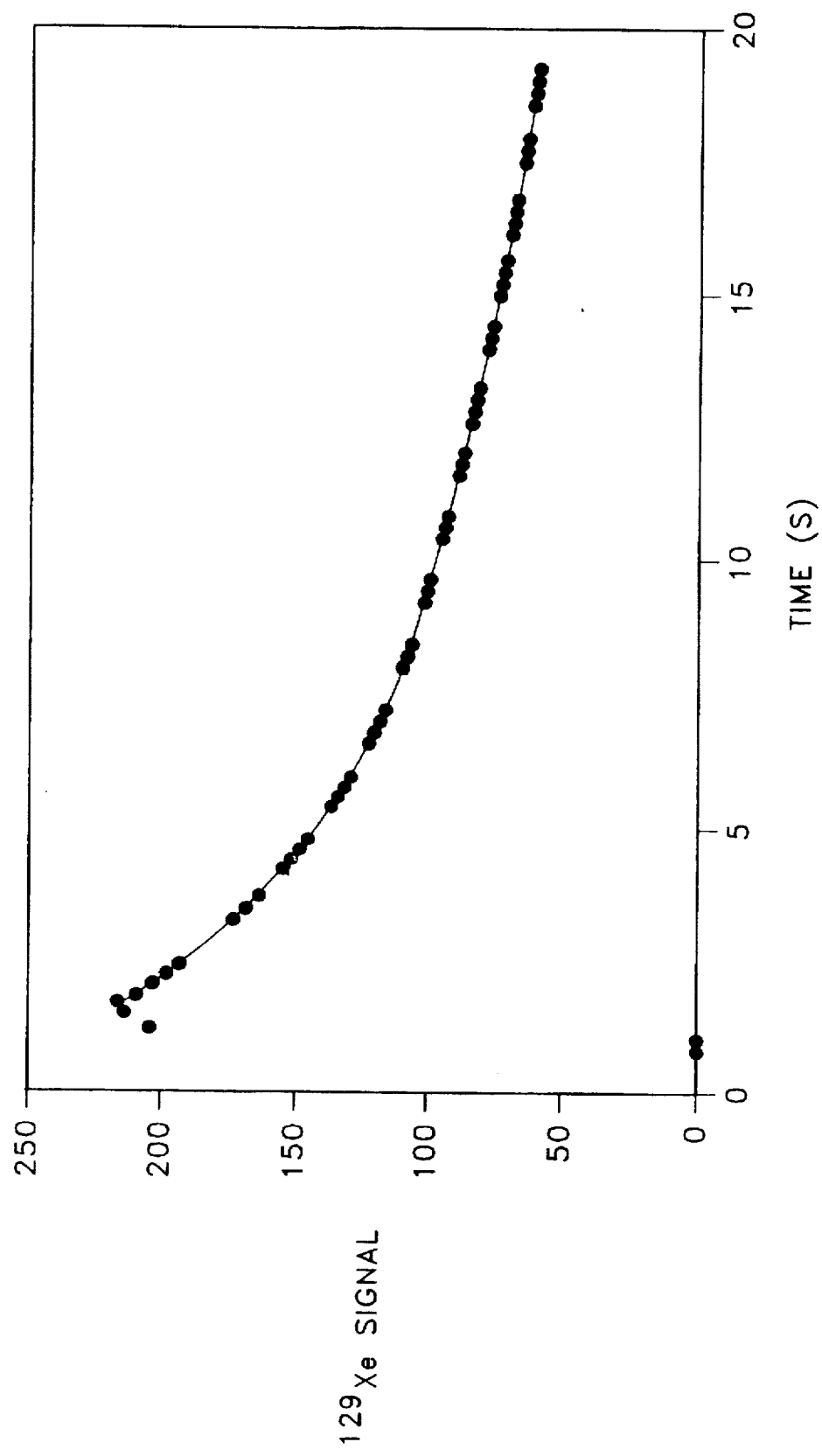
FIG. 6 shows a graph illustrating a decrease in $^{129}$Xe magnetic resonance signal intensity, obtained from mouse lung inflated by hyperpolarized $^{129}$Xe, as a function of time.

FIG. 6 shows the time variation of $^{129}$Xe magnetization in the same lung as that imaged in FIG. 5 after another bolus of hyperpolarized $^{129}$Xe. The decrease in $^{129}$Xe magnetization following the rapid influx of $^{129}$Xe into the lung is distinctly not monoexponential. The curve, decomposed into a sum of two exponentials, allows a value of T$_1$ of approximately 28 s to be extracted from the trailing edge of the decay. The early decrease in intensity probably reflects bulk transfer of $^{129}$Xe out of the lung (deflation to resting volume) rather than magnetization decay. This is evident from the difference between the turgid lung in FIG. 5b (ca. 1 s after Xe release) and the lung in FIG. 5c (7 s later): the lobes have shrunk and the bright trachea has descended. This effect was confirmed visually using boli of N$_2$.

The $^{129}$Xe images shown in FIG. 5 were obtained in 600 ms using a Xenon concentration of approximately 40 mM, a concentration which is tiny compared to the 80–100M concentrations of proton typical of $^1$H$_2$O imaging. Nonetheless, the signal intensities, spatial resolution (<0.3 mm$^3$), and data acquisition rates all exceed those obtained in conventional clinical $^1$H$_2$O-MRI. Moreover, the magnetization densities are so large that several images can be generated in rapid succession, allowing for real-time tracking of physiological processes.

It is believed that these images are the first reported for either Boltzmann or laser polarized $^{129}$Xe. While FIG. 5 demonstrates quite clearly the power of this technique for imaging the lungs, it may turn out that $^3$He, which has a larger magnetic moment, longer gas phase T$_1$ values, (References 60–61), and which is significantly less expensive than $^{129}$Xe, may be the nucleus of choice for lung imaging. However, the features of Xenon which are unmatched by the lighter noble gases, include its good solubility in non-polar solvents and its high electronic polarizability, (Reference 47), which is responsible for the extreme sensitivity of the $^{129}$Xe resonance frequency and relaxation time values to environment. (References 16–17).

Such applications, however, do require that the longitudinal relaxation time of polarized $^{129}$Xe be long compared to the time scales of the processes being studied. The question that immediately arises is whether the T$_1$ of polarized $^{129}$Xe in the lung is long enough to permit transport of sufficient magnetized probe to the various tissues, and whether T$_1$ in these tissues will allow survival of adequate signal for imaging.

While long relaxation times can be attained by laboriously constructing pristine environments such as pumping cells (T$_1$>30 min), biological situations pose a marked departure from such ideal conditions. For instance, as noted above, paramagnetic O$_2$ in the gas phase has been shown to relax $^{129}$Xe with a relaxivity of 0.0087 s$^{-1}$mM$^{-1}$. (Reference 18). Measurements showing that T$_1$≈28 s in the nitrogen flushed lung indicate that this is quite sufficient for lung imaging applications. This is demonstrated by the fact that two images, 7 seconds apart, could be acquired with a single bolus of Xenon. For the case of a live, breathing animal, we can use the O$_2$ relaxivity data to estimate the contribution to relaxation for the component of Oxygen contained in alveolar air (–110 Torr, 5.7 mM). For an animal breathing 40–75% Xenon and 20% O$_2$, we estimate T$_1$ to be on the order of 10–15 s, which is clearly adequate for lung imaging (FIG. 9.3c). Moreover, 12 s represents 5–10 blood circuits in a mouse, (Reference 62), and nearly a full circuit in a human. (Reference 63). Pulmonary blood should receive adequate concentrations of polarized $^{129}$Xe.

The high $^{129}$Xe polarizations attained permit the use of high-speed imaging protocols hitherto limited to $^1$H$_2$O. We note that our field gradients and acquisition programs, conservatively chosen to match standard $^1$H$_2$O protocols, waste both time and $^{129}$Xe magnetization sampling empty voxels. Without any optimization of parameters, the contrast and resolution are already quite adequate. Future optimization of imaging parameters should easily improve upon these early images. Moreover, typical voxel sizes for human specimens, especially under the more exigent restraints of functional imaging, are 3×3×8 mm$^3$, or larger. (Reference 64). This represents a voxel that is 500 times larger than those displayed in FIG. 5. This represents, of course, either 500 fold more $^{129}$Xe spins per voxel or the feasibility of 500 fold dilution of the $^{129}$Xe for equivalent signal intensity.

Though our studies made use of relatively expensive isotopically enriched Xenon (70% $^{129}$Xe), a sacrifice of a factor of only 3 in MR signal would result from the use of inexpensive natural abundance Xenon (26% $^{129}$Xe). Because the polarizations achieved through optical techniques are entirely field-independent. (References 32, 20). MR signals scale only linearly with field. Thus, MRI using laser-polarized gases can be performed at lower magnetic fields with only linear sacrifices in signal intensity (as opposed to the quadratic loss with Boltzmann polarization MR). In fact, the ratio of hyperpolarized to Boltzmann spin excess increases as magnetic field decreases; thus, in a 1 T clinical magnet the ratio is $10^6$.

If the actual relaxation times in different physiological environments turn out to be close to those estimated above, the extension of $^{129}$Xe imaging to other parts of the body should prove to be limitless.

APPENDIUM OF REFERENCES

1. Wyrwicz, A. M., Schofield, J. C., Tillman, P. C., Gordon, R. E., and Martin, P. A., *Science*, 222, 428 (1983).
2. Miller, K. W., Reo, N. V., Uiterkamp, A. J. M. S., Stengle, D. P., Stengle, T. R., and Williamson, K. L., *Proc. Natl. Acad. Sci. USA*, 78, 4946 (1981).
3. Evers, A. S., Berkowitz, B. A., and d'Avignon, D. A., *Nature*, 328, 157 (1987).
4. Wyrwicz, A. M., Li, Y.-E., and Schofield, J. C., *FEBS Lett.*, 162, 334 (1983).
5. Burt, C. T., Moore, R. R., Roberts, M. F., and Brady, T. J., *Biochim. Biophys. Acta*, 805, 375 (1984).
6. Burt, C. T., Moore, R. R., and Roberts, M. F., *J. Magn. Reson.*, 53, 163 (1983).
7. Lockhart, S. H., Cohen, Y., Yasuda, N., Kim, F., Litt, L., Eger, E. I., Chang, L.-H., and James, T., *Anesthesiology*, 73, 455 (1990).
8. Mason, J., in *Multinuclear NMR*, eds. Mason, J., p. 606–607, Plenum Press, New York (1987).
9. Barany, M., Spigos, D. G., Mok, E., Venkatasubramanian, P. N., Wilbur, A. C., and Langer, B. G., *Magn. Reson. Imaging*, 5, 393 (1987).
10. Fullerton, G. D., and Cameron, I. L., in *Biomedical Magnetic Resonance Imaging: Principles. Methodology, and Applications*, eds. Wehrli, F. W., Shaw, D. S., and Kneeland, J. B., p. 115–155, VCH Publishers, New York (1988).
11. Susskind, H., Atkins, H. L., Klopper, J. K., Ansari, A. N., Richards, P., and Fairchild, R. G., *Prog. Nucl. Med.*, 5, 144 (1978).
12. Susskind, H., Ellis, K. J., Atkins, H. L., Cohn, S. H., and Richards, P., *Proc. Nucl. Med.*, 5, 13 (1978).
13. Kendall, B. E., and Moseley, I. F., *J. Neuroradiology*, 8, 3 (1981).
14. Imai, A., Meyer, J. S., Kobari, M., Ichijo, M., Shinohara, T., and Oravez, W. T., *Neuroradiology*, 30, 463 (1988).
15. Yonas, H., Sekhar, L., Johnson, D. W., and Gur, D., *Neurosurgery*, 24, 368 (1989).
16. Albert, M. S., Springer, C. S., Murphy, R., and Wishnia, A., *Abs.*, 11th *Ann. Mtg. Soc. Magn. Reson. Med.*, 2104 (1992).
17. Albert, M. S., Springer, C. S., and Wishnia, A., *Abs.*, 11th *Ann. Mtg. Soc. Magn. Reson. Med.*, 4710 (1992).
18. Jameson, C. J., Jameson, A. K., and Hwang, J. K., *J. Chem. Phys.*, 89, 4074 (1988).
19. Carver, T. R. *Science*, 141, 599 (1963).
20. Happer, W., Miron, E., Schaefer, S., Schreiber, D., van Wijngaarder, W. A., and Zeng, X., *Phys. Rev. A*, 29, 3092 (1984).
21. Wagshul, M. E. and Chupp, T. E., *Phys. Rev. A*, 40, 4447 (1989).
22. Wagshul, M. E., Thesis, The Department of Physics, Harvard University (1991).
23. Grover, B. C., *Phys. Rev. Lett.*, 40, 391 (1978).
24. Schaefer, S. R., Cates, G. D., Chien, T. -R., Gonatas, D., Happer, W., and Walker, T. G., *Phys. Rev. A*, 39, 5613 (1989).
25. Schaefer, S. R., Cates, G. D., and Happer, W., *Phys. Rev. A*, 41, 6063 (1990).
26. Schearer, L. D., in *Phys. Rev. Lett.*, 21, 660 (1968).
27. Schearer, L. D., in *Phys. Rev.*, 188, 505 (1969).
28. Schearer, L. D., in *Phys. Rev.*, 180, 83 (1969).
29. Colegrove, F. D., Schearer, L. D., and Walters, G. K., *Phys. Rev.*, 132, 2561 (1963).
30. Hadeishi, T., and Liu, C.-H., *Phys. Rev. Lett.*, 19, 211 (1967).
31. Schearer, L. D., *Phys. Lett.*, 28A, 660 (1969).
32. Cates, G. D., Benton, D. R., Gatzke, M., Happer, W., Hasson, K. C., and Newbury, N. R., *Phys. Rev. Lett.*, 65, 2591 (1990).
33. Gatzke, M., Cates, G. D., Driehuys, B., Fox, D., Happer, W., and Saam, B., *Phys. Rev. Lett.*, 70, 690 (1993).
34. Bhaskar, N. D., Happer, W., and McClelland, T., *Phys. Rev. Lett.*, 49, 25 (1982).
35. Cates, G. D., Fitzgerald, R. J., Barton, A. S., Bogorad, P., Gatzke, M., Newbury, N. R., and Saam, B., *Phys. Rev. A*, 45, 4631 (1992).
36. Raftery, D., Long, H., Meersmann, T., Grandinetti, P. J., Reven, L., and Pines, A., *Phys. Rev. Lett.*, 66, 584 (1991).
37. Raftery, D., Long, H., Reven, L., Tang, P., and Pines, A., *Chem. Phys. Lett.*, 191, 385 (1992).
38. Long, H. W. Gaede, H. C., Shore, J., Reven, L., Bowers, C. R., Kritzenberger, J., Pietrass, T., and Pines, A., *J. Am. Chem. Soc.*, 115, 8491 (1993).
39. Rinck et al., *An Introduction to Magnetic Resonance in Medicine* (1990).
40. Stark et al., eds., *Magnetic Resonance Imaging*, Vol. 1, 2d ed. (1992).
41. Hunt E. R., and Carr, H. Y., *Phys. Rev.*, 130, 2302 (1963).
42. Tilton, R. F., and Kuntz, I. D., *Biochemistry*, 21, 6850 (1982).
43. Diehl, P., and Jokisaari, J., *J. Magn. Reson.*, 88, 669 (1990).
44. Cullin, S. C., and Gross, E. G., *Science*, 113, 580 (1951).
45. Wilcock, R. J., Battino, R., Danforth, W. F., and Wilhelm, E., *J. Chem. Thermodyn.*, 10, 317 (1978).
46. Blumgart, H. L., and Weiss, S., *J. Clin. Invest.*, 4, 339–425 (1927).
47. Pollack, G. L., Himm, J. F., and Enyeart, J. J., *J. Chem. Phys.*, 81, 3239 (1984).
48. Wishnia, A., *Biochemistry*, 8, 5064 (1969).
49. Bouchiat M. A., Carver T. R., and Varnum C. M., *Phys. Rev. Lett.*, 5, 373 (1960).
50. Zeng, X., Wu, Z., Call, T., Miron, E., Schreiber, D., and Happer, W., *Phys. Rev. A*, 31, 260 (1985).
51. Laloe, F., Nacher, P. J., Leduc, M., and Schearer, L. D., *AIP Conf. Proc.* #131 (Workshop on Polarized $^3$He Beams and Targets) (1984).
52. Ernst et al., *Principles of Nuclear Magnetic Resonance in One and Two Dimensions* (1987).
53. Wehrli, S. W., et al., eds., *Biomedical Magnetic Resonance Imaging* (1988).
54. Schoenborn, B. P., *Nature*, 208, 760 (1965).
55. Moschos, A., and Reisse, J., *J. Mag. Reson.*, 95, 603 (1991).
56. Yonas, H., Laligam, S., Johnson, D. W., and Gur, D., *Neurosurgery*, 24, 368 (1989).
57. Kendall, B. E., and Moseley, I. F., *J. Neuroradiology*, 8, 3 (1981).
58. Haase, A., Frahm, J., Matthaei, D., Hanicke, W., and Merboldt, K. D., *J. Magn. Reson.*, 67, 217 (1986).

59. Look, D. C., and Locker, D. R., *Rev. Sci. Instrum.*, 41, 250–251 (1970).
60. Norberg, R. E., in *Rare Gas Solids*, eds. Hohler, G., Springer-Verlag, New York (1984).
61. Yen, W. M., and Norberg, R. E., *Phys. Rev.*, 131, 269 (1963).
62. Kaplan, H. M., Brewer, N. R., and Blair, W. H., in *The Mouse in Biomedical Research*, eds. Foster, H. L., Small, J. D., and Fox, J. G., p. 248–278, Academic Press, New York (1983).
63. Knudsen, G. M., Pettigrew, K. D., Patlak, C. S., and Paulson, O. B., *Am. J. Physiol.*, In Press.
64. Kanal, E., and Wehrli, F. W., in *Biomedical Magnetic Imaging*, eds. Wehrli, F. W., Shaw, D., and Kneeland, J. B., p. 47–112, VCH Publishers, New York (1988).

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. Apparatus for nuclear magnetic resonance imaging, which comprises:
   a) means for imaging a spatial distribution of a hyperpolarized noble gas by NMR; and
   b) means for providing imageable quantities of said hyperpolarized noble gas to a sample to be imaged by said imaging means.

2. The apparatus of claim 1, wherein said providing means further comprises means for hyperpolarizing said noble gas to generate a hyperpolarized noble gas.

3. The apparatus of claim 2, wherein said hyperpolarizing means includes means for hyperpolarizing said noble gas by spin exchange with an alkali metal.

4. The apparatus of claim 2, wherein said hyperpolarizing means includes means for hyperpolarizing said noble gas by metastability exchange.

5. The apparatus of claim 1, wherein said providing means further comprises means for storing said at least one hyperpolarized noble gas.

6. The apparatus of claim 1, wherein said hyperpolarized noble gas includes hyperpolarized Helium-3 or hyperpolarized Xenon-129.

7. A medical composition, comprising a medically acceptable bifunctional gas effective for concurrent in vivo anesthesiological and magnetic resonance imaging functions, wherein the bifunctional gas comprises at least one hyperpolarized noble gas.

8. The medical composition of claim 7, wherein said bifunctional gas further comprises a medically acceptable carrier gas.

9. The medical composition of claim 7, wherein said hyperpolarized noble gas comprises hyperpolarized Xenon-129.

* * * * *

UNITED STATES PATENT AND TRADEMARK OFFICE
CERTIFICATE OF CORRECTION

PATENT NO.  : 5,789,921
DATED       : August 4, 1998
INVENTOR(S) : Albert et al.

It is certified that error appears in the above-identified patent and that said Letters Patent is hereby corrected as shown below:

On the title page, Item [62]

Division of Ser. No.: Chnage "1995" to "1994.

Signed and Sealed this

Twenty-third Day of February, 1999

Attest:

Q. TODD DICKINSON

*Attesting Officer*         *Acting Commissioner of Patents and Trademarks*